(12) United States Patent
Kim et al.

(10) Patent No.: US 11,080,891 B2
(45) Date of Patent: Aug. 3, 2021

(54) METHOD AND SYSTEM FOR DETECTING DANGEROUS SITUATION

(71) Applicant: SAMSUNG ELECTRONICS CO., LTD., Suwon-si (KR)

(72) Inventors: Joo-young Kim, Suwon-si (KR); Joon-ho Kim, Seongnam-si (KR); Do-jun Yang, Yongin-si (KR); Hyun-woo Lee, Seoul (KR); Jong-hee Han, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 95 days.

(21) Appl. No.: 15/901,272

(22) Filed: Feb. 21, 2018

(65) Prior Publication Data

US 2018/0342081 A1    Nov. 29, 2018

Related U.S. Application Data

(60) Provisional application No. 62/511,013, filed on May 25, 2017.

(30) Foreign Application Priority Data

Sep. 5, 2017    (KR) .................. 10-2017-0113344

(51) Int. Cl.
*A61B 5/11*    (2006.01)
*G06T 7/73*    (2017.01)
(Continued)

(52) U.S. Cl.
CPC ............ *G06T 7/75* (2017.01); *G06K 9/00335* (2013.01); *G06K 9/00771* (2013.01);
(Continued)

(58) Field of Classification Search
CPC combination set(s) only.
See application file for complete search history.

(56) References Cited

U.S. PATENT DOCUMENTS 7,110,569 B2 *    9/2006    Brodsky ............ G06K 9/00335
348/169
2005/0285941 A1 *    12/2005    Haigh .............. G08B 13/19602
348/155

(Continued)

FOREIGN PATENT DOCUMENTS

CN        106991790 A       7/2017
JP        WO2012/004907 A1  1/2012
(Continued)

OTHER PUBLICATIONS

Communication dated Sep. 27, 2018 issued by the International Searching Authority in Counterpart Application No. PCT/KR2018/006981 (PCT/ISA/220, PCT/ISA/210, and PCT/ISA/237).

(Continued)

*Primary Examiner* — Jeffery A Williams
(74) *Attorney, Agent, or Firm* — Sughrue Mion, PLLC

(57) ABSTRACT

A method of detecting a dangerous situation includes obtaining a first image including a first object capable of generating a movement, by using a dynamic vision sensor (DVS); detecting, from the first image, a second image including the first object in a predefined pose; and determining whether a situation of the first object is the dangerous situation by analyzing the second image.

17 Claims, 27 Drawing Sheets

(51) Int. Cl.
*G06K 9/00* (2006.01)
*G08B 21/04* (2006.01)

(52) U.S. Cl.
CPC ....... *G08B 21/043* (2013.01); *G08B 21/0476* (2013.01); *G06T 2207/30196* (2013.01)

(56) References Cited

U.S. PATENT DOCUMENTS

| | | | |
|---|---|---|---|
| 2008/0043144 A1* | 2/2008 | Amir | G06K 9/00711 348/469 |
| 2008/0232643 A1* | 9/2008 | Leichter | G06T 7/277 382/103 |
| 2009/0315996 A1* | 12/2009 | Guler | G01S 3/7864 348/169 |
| 2012/0151601 A1 | 6/2012 | Inami et al. | |
| 2014/0320706 A1 | 10/2014 | Shin et al. | |
| 2015/0302710 A1 | 10/2015 | Jin et al. | |
| 2016/0217326 A1 | 7/2016 | Hosoi | |
| 2017/0061763 A1* | 3/2017 | Hanson | G06T 7/194 |
| 2017/0109990 A1 | 4/2017 | Xu et al. | |
| 2017/0124410 A1 | 5/2017 | Cho et al. | |
| 2018/0027186 A1* | 1/2018 | Jung | H04N 13/20 348/333.05 |
| 2018/0122099 A1 | 5/2018 | Lee | |

FOREIGN PATENT DOCUMENTS

| | | |
|---|---|---|
| JP | 2016-187176 A | 10/2016 |
| JP | 2017-016589 A | 1/2017 |
| KR | 10-2008-0101402 A | 11/2008 |
| KR | 10-2012-0114629 A | 10/2012 |
| KR | 101365237 B1 | 2/2014 |
| KR | 10-1454548 B1 | 10/2014 |
| KR | 10-2016-0037326 A | 4/2016 |
| KR | 10-2016-0116075 A | 10/2016 |
| KR | 101704471 B1 | 2/2017 |
| KR | 10-2017-0050293 A | 5/2017 |
| WO | 2016/053886 A1 | 4/2016 |

OTHER PUBLICATIONS

Communication dated Aug. 31, 2018 issued by the Korean Patent Office in Counterpart Korean Application No. 10-2017-0113344.
Belbachir et al., "Event-driven Stereo Vision for Fall Detection", Computer Vision and Pattern Recognition Workshops, Aug. 12, 2011, pp. 78-83.
Jiseob Kim et al., "2D Image-based Integrated Human Pose, Action, Location Recognition System using Deep Convolution Neural Network", Korea Information Science Society, Jun. 2015, 4 pages.
Communication dated Mar. 19, 2019, issued by the Korean Intellectual Property Office in counterpart Korean Application No. 10-2017-0113344.
Communication dated May 17, 2019, issued by the Korean Intellectual Property Office in counterpart Korean Application No. 10-2017-0113344.
Communication dated Apr. 3, 2020, from the European Patent Office in counterpart European Application No. 18853299.8.
Ahmed Nabil Belbachir et al. "Event-driven Feature Analysis in a 4D Spatiotemporal Representation for Ambient Assisted Living" IEEE International Conference on Computer Vision Workshops, 2011, (pp. 1570-1577).
Zhengming Fu et al. "An address-Event Fall Detector for Assisted Living Applications" IEEE Transactions on biomedical circuits and systems, vol. 2, No. 2, Jun. 2008 (pp. 88-96).
Martin Humenberger et al. "Embedded Fall Detection with a Neural Network and Bio-Inspired Stereo Vision" IEEE, Jun. 16, 2012, (pp. 60-67).
Communication dated Oct. 8, 2020, issued by the Korean Intellectual Property Office in corresponding Korean Application No. 10-2019-0101309.
Communication dated May 31, 2021 issued by the State Intellectual Property Office of P.R. China in counterpart Chinese Application No. 201880057012.4.
Communication dated Apr. 13, 2021 issued by the Japanese Intellectual Property Office in counterpart Japanese Application No. 2020-513299.

* cited by examiner

FIG. 3
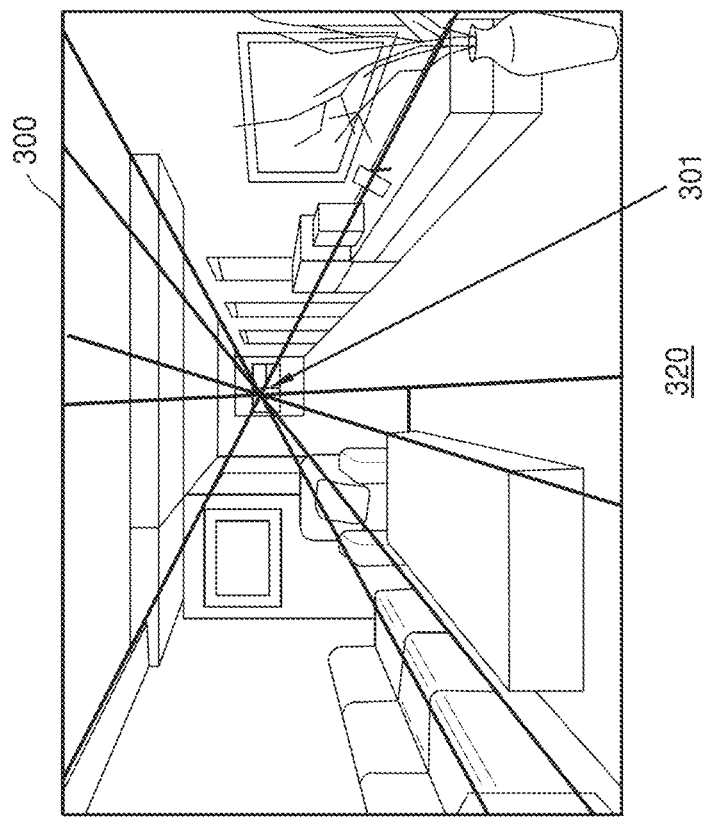
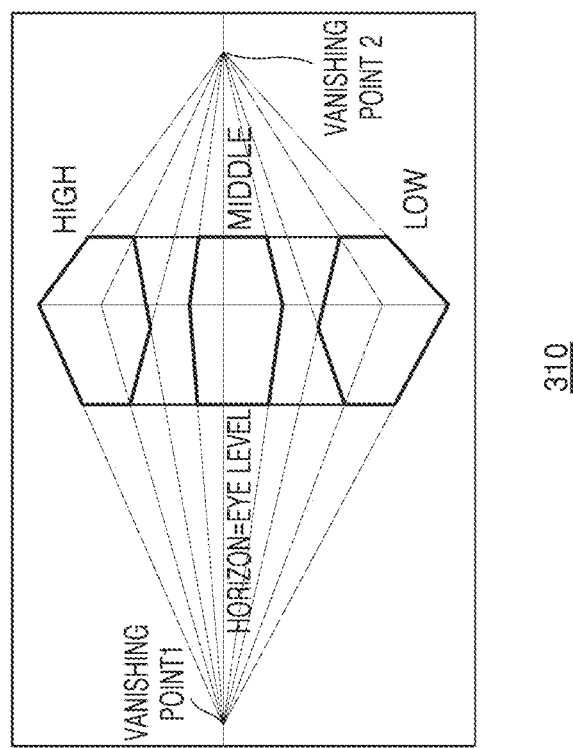

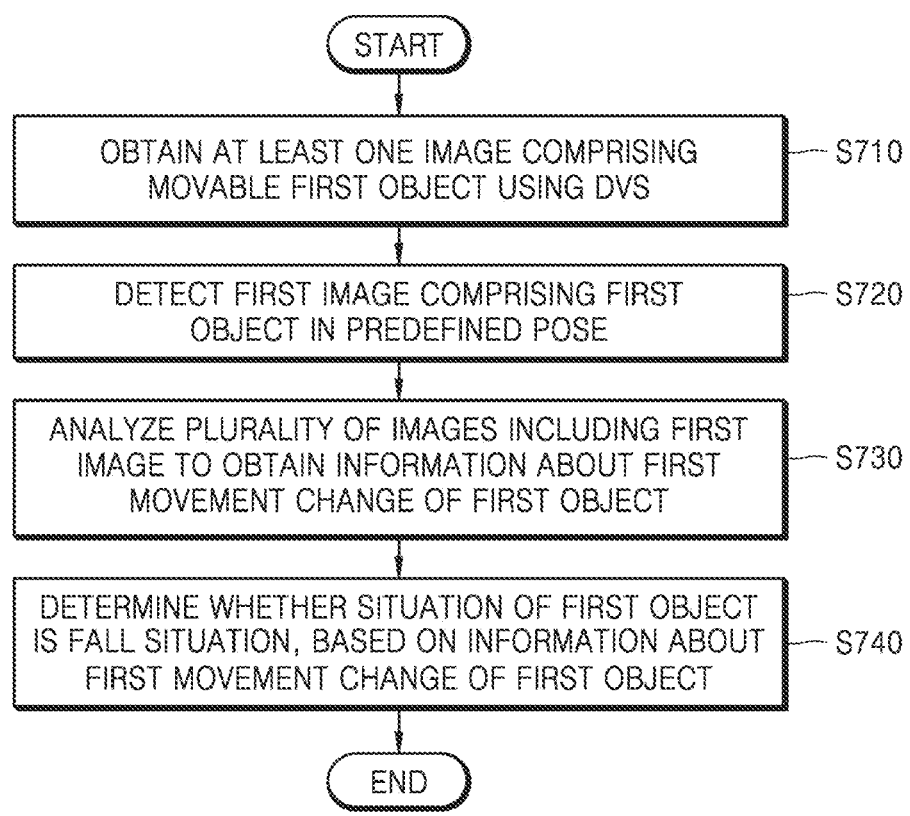

METHOD AND SYSTEM FOR DETECTING DANGEROUS SITUATION

CROSS-REFERENCE TO RELATED APPLICATIONS

This application claims the benefit of U.S. Provisional Application No. 62/511,013, filed on May 25, 2017, in the US Patent Office, and priority from Korean Patent Application No. 10-2017-0113344, filed on Sep. 5, 2017, in the Korean Intellectual Property Office, the disclosures of which are incorporated herein by reference in their entireties.

BACKGROUND

1. Field

Methods and apparatuses consistent with example embodiments relate to a method and system for detecting a dangerous situation (e.g., a fall) by using a dynamic vision sensor (DVS).

2. Description of the Related Art

A fall refers to an object falling down or getting hurt in a fall and usually occurs in the elderly, but the fall may occur in all ages. In particular, the occurrence of falls among the elderly is increasing, and may be accompanied by serious injury or death due to fall complications.

In addition to death due to falls, falls among the elderly result in a significant decrease in quality of life due to severe injuries. 20%-30% of older people that go to a hospital because of a fall suffer from bruises, hip fractures, and/or head damage from the falls. Falls are the biggest cause of trauma among the elderly and are expected to continue to increase with an increase in the number of elderly.

61.5% of falls occur in residential facilities, followed by roads (20.0%) and commercial facilities (18.5%). About 95% of falls in residential facilities occur at home, and 25% to 45% of dangerous environmental factors, such as slippery floors and stairs, are at home. In particular, 20.6% of the falls occur in residential facilities due to slipping on wet surfaces, and 74.3% of falls that occur in the restroom are related to water on the floor.

Therefore, there is a need for a system that accurately detects the presence or absence of a fall occurrence and accurately predicts a risk associated with falls.

SUMMARY

According to an aspect of an example embodiment, there is provided a method of detecting a dangerous situation, the method including: obtaining a first image including a first object capable of generating a movement, by using a dynamic vision sensor (DVS); detecting, from the first image, a second image including the first object in a predefined pose; and determining whether a situation of the first object is the dangerous situation by analyzing the second image.

The detecting of the second image and the determining of whether the situation of the first object is the dangerous situation may be performed by a learning network model.

The detecting of the first image may include: in response to the movement of the first object being detected, comparing a pose of the first object included in the first image with the predefined pose by using the learning network model; and detecting the second image based on a result of the comparing.

The method may further include, in response to the situation of the first object being determined to be the dangerous situation, obtaining a third image including surrounding environment information of the first object generated by moving the DVS with a vibrator; and determining a danger of the first object by analyzing the third image.

The determining of the danger of the first object may include: in response to determining that the movement of the first object is less than a threshold value for a predetermined time, raising a danger level of the first object.

The determining of whether the situation of the first object is the dangerous situation may include: obtaining information about a first movement variation of the first object by analyzing a plurality of images with respect to the first object in the second image; and determining whether the situation of the first object is a fall situation based on the information about the first movement variation of the first object.

The detecting of the second image may include: compensating for a body shape of the first object or a size of the first object included in the first image, by adjusting for at least one from among an angle and a position at which the DVS is installed; and comparing a pose of the first object having the compensated body shape or size with the predefined pose.

The detecting of the second image may include: in response to determining that the first object is partially covered by another object, obtaining a third image including surrounding environment information of the first object generated by moving the DVS with a vibrator; detecting, based on the third image, a second object covering a part of the first object in the third image; and estimating a pose of the first object partially covered by the second object by adjusting for the second object.

The obtaining of the first image may include: adjusting a degree of definition of the first object included in the first image according to a privacy level of a space in which the DVS is installed.

The obtaining of the first image may include: obtaining the first image in a high resolution mode in response to the movement of the first object being detected; and obtaining the first image in a low resolution mode in response to the movement of the first object not being detected.

According to an aspect of another example embodiment, there is provided a method of detecting a dangerous situation, the method including: obtaining a first image including a first object capable of generating a movement, by using a dynamic vision sensor (DVS); detecting, from the first image, a second image including the first object in a predefined pose; in response to the second image being detected, obtaining a third image including surrounding environment information of the first object generated by moving the DVS with a vibrator; and determining whether a situation of the first object is the dangerous situation by analyzing the third image.

The detecting of the second image and the determining of whether the situation of the first object is the dangerous situation may be performed by a learning network model.

According to an aspect of another example embodiment, there is provided a device for detecting a dangerous situation, the device including: a dynamic vision sensor (DVS) configured to obtain a first image including a first object capable of generating a movement; and a processor configured to: detect, from the first image, a second image including the first object in a predefined pose, and analyze the second image to determine whether a situation of the first object is the dangerous situation.

The processor may be further configured to detect the second image by using a learning network model, and determine whether the situation of the first object is the dangerous situation by using the learning network model.

The device may include a vibrator configured to move the DVS, wherein the processor may be further configured to: control the vibrator to move the DVS in response to determining that the situation of the first object is the dangerous situation; obtain a third image including surrounding environment information of the first object generated by moving the DVS; and analyze the third image to determine a danger of the first object.

The processor may be further configured to raise a danger level of the first object in response to determining that a movement of the first object is less than a threshold value for a predetermined time.

The processor may be further configured to compensate for a body shape of the first object or a size of the first object included in the first image, by adjusting for at least one from among an angle and a position at which the DVS is installed, and compare a pose of the first object having the compensated body shape or size with the predefined pose to detect the second image.

The device may include a vibrator configured to move the DVS, wherein the processor may be further configured to: obtain a third image including surrounding environment information of the first object generated by moving the DVS with the vibrator in response to determining that the first object is partially covered by another object; detect a second object covering a part of the first object, based on the third image; and estimate a pose of the first object partially covered by the second object by adjusting for the second object.

According to an aspect of another example embodiment, there is provided a device for detecting a dangerous situation, the device including: a dynamic vision sensor (DVS) configured to obtain a first image including a first object capable of generating a movement; a vibrator configured to move the DVS; and a processor configured to: detect a second image including the first object in a predefined pose from the first image and analyze the second image; in response to the second image being detected, obtain a third image including surrounding environment information of the first object generated by moving the DVS with the vibrator; and analyze the third image to determine whether a situation of the first object is the dangerous situation.

According to an aspect of another example embodiment, there is provided a non-transitory computer-readable storage medium storing instructions for causing a computer to: obtain a first image including a first object capable of generating a movement, by using a dynamic vision sensor (DVS); detect a second image including the first object in a predefined pose from the first image; and determine whether a situation of the first object is a dangerous situation by analyzing the second image.

The instructions may cause the computer to: obtain a third image including surrounding environment information of the first object generated by moving the DVS; analyze the third image to determine a danger of the first object; and generate a fall danger map that displays a relative danger of a plurality of areas in the surrounding environment.

The instructions may further cause the computer to: determine a privacy level of a space in which the DVS is installed; and in response to determining that the privacy level is high, adjust a degree of definition of the first object included in the first image to be low definition; and in response to determining that the privacy level is low, adjust a degree of definition of the first object included in the first image to be high definition.

The instructions may further cause the computer to: obtain information about a first movement variation of the first object by analyzing a plurality of images with respect to the first object in the second image; and determine a similarity between the first movement change of the first object and a second movement change representing a previously stored fall; and in response to the similarity being greater than a threshold value, determine that the situation of the first object is a fall situation; and in response to similarity being less than or equal to the threshold value, determine that the situation of the first object is not the fall situation.

BRIEF DESCRIPTION OF THE DRAWINGS

These and/or other aspects will become apparent and more readily appreciated from the following description of the example embodiments, taken in conjunction with the accompanying drawings in which:

FIG. 3 is a diagram illustrating an operation of obtaining space information by using vanishing point analysis, according to an example embodiment;

FIG. 7 is a flowchart of a method of detecting a fall, according to an example embodiment;

DETAILED DESCRIPTION

Figure 1:
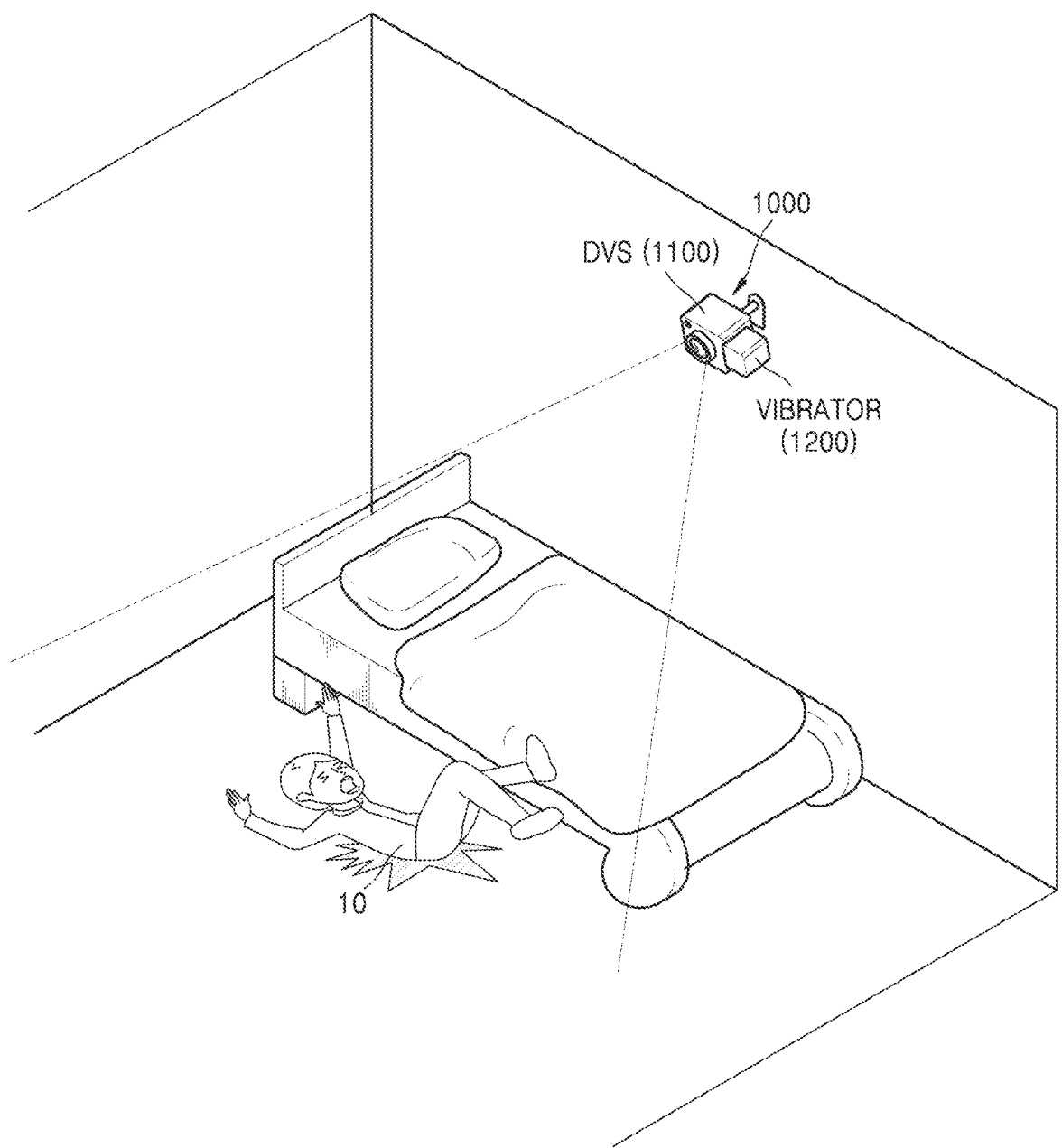
FIG. 1 is a diagram illustrating a system for detecting a dangerous situation, according to an example embodiment.

Example embodiments provide a system for efficiently detecting a dangerous situation (for example, a fall) by analyzing an image obtained by a dynamic vision sensor step by step using a plurality of image processing models.

Example embodiments provide a method and system for detecting a dangerous situation that accurately detect a dangerous situation (e.g., a fall) of an object and predict a risk to the object by using a dynamic vision sensor and a vibrator.

Additional aspects will be set forth in part in the description which follows and, in part, will be apparent from the description, or may be learned by practice of the example embodiments.

The terms used in the specification will be schematically described, and then, the example embodiments will be described in detail.

The terms used in this specification are those general terms currently widely used in the art, but the terms may vary according to the intention of those of ordinary skill in the art, precedents, or new technology in the art. Also, specified terms may be selected by the applicant, and in this case, the detailed meaning thereof will be described in the detailed description. Thus, the terms used in the specification should be understood not as simple names but based on the meaning of the terms and the overall description.

Throughout the specification, it will also be understood that when a component "includes" an element, unless there is another opposite description thereto, it should be understood that the component does not exclude another element but may further include another element. Also, terms such as " . . . unit", " . . . module", or the like refer to units that perform at least one function or operation, and the units may be implemented as hardware or software or as a combination of hardware and software.

In the present specification, the term "fall" may mean a phenomenon in which a specific object falls or falls and gets hurt.

Reference will now be made in detail to example embodiments, which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

FIG. 1 is a diagram illustrating a system for detecting a dangerous situation according to an example embodiment.

Referring to FIG. 1, the system for detecting the dangerous situation according to an example embodiment may include a device for detecting the dangerous situation. The dangerous situation may mean that an object (e.g., a person or animal) capable of generating a movement is in an emergency situation or an imminent situation. The dangerous situation may mean a situation in which the object is injured. For example, the dangerous situation may vary, such as a situation in which an object falls, a situation in which a fire occurs in a space including the object, a situation in which a flood occurs, a situation in which a landslide occurs, or a situation in which gas leaks. Hereinafter, the case where situation in which the object falls will be described as an example.

According to an example embodiment, the device for detecting the dangerous situation may include a fall detection device 1000. The fall detecting device 1000 may be a device that obtains at least one image (frame) for an object 10 and detects a fall of the object 10 using the obtained at least one image (frame). According to an example embodiment, the object 10 may be a movable person, animal, or the like, but is not limited thereto. According to an example embodiment, a fall detection device 1000 may designate a detection target as a specific object based on an input of a user. For example, the fall detection device 1000 may designate a fall detection target as only human, with the exception of animal. Also, the fall detection device 1000 may designate a specific person as a monitoring target. For example, when a mother, a father, a grandfather, and a child are present at home, the grandfather may be designated as the fall detection target.

According to an example embodiment, the fall detection device 1000 may include a dynamic vision sensor (DVS) 1100 and a vibrator 1200.

The DVS 1100 is an image sensor that adopts a way a person's iris receives information and is a sensor capable of obtaining image data of a moving object. For example, the DVS 1100 transmits image data to a processor only when there is a local change in movement in pixel units. That is, the DVS 1100 may transmit image data to the processor only when a moving event occurs. Accordingly, the DVS 1100 does not process data when an object is stopped, measures the moving object only when the object moves, and transmits data to the processor, thereby preventing waste of data caused by general image sensors continuously sending frames to an image processor.

The DVS 1100 may solve a problem that a general visual recognition system is vulnerable to rapid movement. The DVS 1100 may overcome a blur phenomenon because the DVS 1100 receives data on a per-pixel basis instead of receiving the data in frame units.

Also, the DVS 1100 may have a resolution in microseconds. In other words, the DVS 1100 may have a temporal resolution (e.g., a super high speed frame>1K FPS) better than a super high-speed camera that shoots thousands of frames per second. In addition, the DVS 1100 has dramatically reduced power consumption and data storage requirements, resulting in a dramatic increase in a dynamic range (a range of brightness identifiable by a sensor).

On the other hand, since an image obtained by the DVS 1100 is represented only by an outline of the moving object 10, the DVS 1100 may also be useful for protecting privacy of the object 10 to be monitored. Also, the DVS 1100 may detect the movement of the object 10 when only a slight amount of light is present even in a dark place.

According to an example embodiment, the DVS 1100 may periodically obtain an image, and the fall detection device 1000 may use the image obtained periodically in the DVS 1100 to monitor whether the object 10 falls. For example, when the object 10 falls from a bed, the DVS 1100 may detect a movement of the object 10 falling from the bed. At this time, the fall detection device 1000 may use a plurality of deep learning models step by step to efficiently determine whether the object 10 falls. For example, the fall detection device 1000 does not analyze a moving image from the beginning, but performs a moving image analysis only when a static image includes the object 10 in a pose related to fall, thereby reducing consumption of computation resources. An operation of the fall detection device 1000 efficiently determining whether the object 10 falls will be described in detail later with reference to FIGS. 7 and 8A.

The vibrator 1200 may be a device for generating vibration. For example, the vibrator 1200 may be a vibration motor that outputs a vibration signal.

According to an example embodiment, the vibrator 1200 may generate vibrations to move the DVS 1100 artificially. The DVS 1100 is an image sensor useful for movement change detection, but may not obtain information when there is no movement. Accordingly, the vibrator 1200 may artificially move the DVS 1100 so that the DVS 1100 may obtain images of objects even in the absence of movement of the objects.

The vibrator 1200 may be positioned proximate to the DVS 1100 so that vibration may be transmitted to the DVS 1100. For example, the vibrator 1200 may be attached to the DVS 1100. The vibrator 1200 may be located within a housing with the DVS 1100.

According to an example embodiment, the vibrator 1200 may output a vibration signal when a specific event occurs. For example, the vibrator 1200 may output the vibration signal when the fall detection device 1000 is booted, an occlusion is detected, or a situation of the object 10 is determined as a fall situation. The occlusion may mean that the moving object 10 is partially or wholly covered by another object. An operation of the vibrator 1200 outputting the vibration signal will be described in more detail with reference to FIG. 2.

According to an example embodiment, the system for detecting the dangerous situation may further include a server. In this case, the server may receive fall detection information of the object 10 from the fall detection device 1000. The server may verify the received fall detection information, or may transmit a warning message to an external device according to the fall detection information.

According to an example embodiment, the fall detection device 1000 may directly generate deep learning models for confirming whether a fall occurs, or may receive the deep learning models from the server. The deep learning models may be one of, but are not limited to, a supervised learning model, an unsupervised learning model, and a reinforcement learning model. The fall detection device 1000 may apply images collected from the DVS 1100 to the deep learning models to determine whether the object 10 falls. Meanwhile, according to an example embodiment, the fall detection device 1000 may request the server to determine whether the object 10 falls while transmitting the images collected through the DVS 1100 to the server. For convenience of description, the case where the system for detecting the dangerous situation does not include the server will be described first as an example.

Hereinafter, an operation of the fall detection device 1000 obtaining space information around the fall detection device 1000 at an initial installation stage will be described with reference to FIG. 2.

Figure 2:
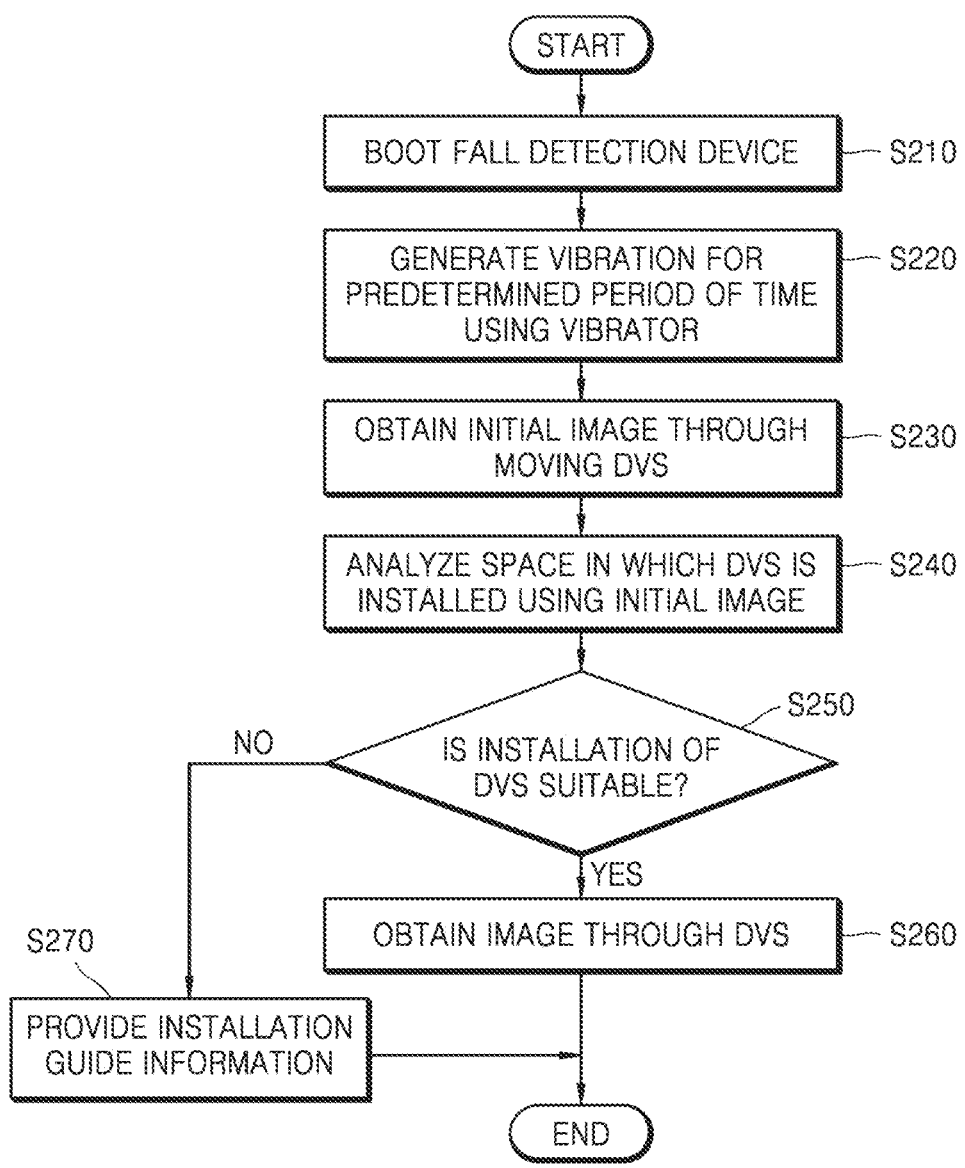
FIG. 2 is a flowchart of a method in which a fall detection device obtains space information by using an initial image upon booting, according to an example embodiment.

FIG. 2 is a flowchart illustrating a method in which the fall detection device 1000 obtains space information using an initial image upon booting according to an example embodiment.

In operation S210, after the DVS 1100 is installed in a specific space, the fall detection device 1000 may boot. According to an example embodiment, the DVS 1100 may be installed at home, office, or hospital, but is not limited thereto. The fall detection device 1000 may be installed outdoors. For example, the fall detection device 1000 may be installed in a mountain where a fall accident occurs frequently.

In operation S220, the fall detection device 1000 may generate vibrations for a certain period of time using the vibrator 1200 upon booting. At this time, the vibration generated in the vibrator 1200 may move the DVS 1100. When the DVS 1100 moves, since relative movement occurs in objects, an image of the objects may be captured regardless of whether the objects are moving.

In operation S230, the fall detection device 1000 may obtain an initial image through the moving DVS 1100. For example, when the DVS 1100 is installed in a main room, the DVS 1100 may obtain an initial image of the main room. At this time, the moving DVS 1100 may obtain images of a wardrobe, a drawer, a desk, a chair, etc., which do not move in the main room. According to an example embodiment, the initial image may be a static image or a moving image.

In operation S240, the fall detection device 1000 may analyze the space where the DVS 1100 is installed (or a space recognized by the DVS 1100) using the initial image. For example, the fall detection device 1000 may check an angle, a position, a height, and a recognition range of the DVS 1100 using a vanishing point of the initial image.

Referring to 310 of FIG. 3, the fall detection device 1000 may analyze the space where the DVS 1100 is installed through vanishing point analysis. A series of parallel lines in a three-dimensional space converge and encounter a point on an image when projected into a two-dimensional space obtained by the DVS 1100. This point is called the vanishing point (e.g., vanishing point 1, vanishing point 2). The fall detection device 1000 may determine a relative height (e.g., upper, middle, or lower) of the installed DVS 1100, a relative position (e.g., left or right), a relative distance from a specific object, etc.

For example, referring to 320 of FIG. 3, the fall detection device 1000 may obtain an image 300 of a living room in which the DVS 1100 is installed through the moving DVS 1100. The fall detection device 1000 may extract a vanishing point 301 using parallel lines on the image 300 of the living room. Objects closer to the vanishing point 301 may be objects farther away from the DVS 1100. It may be seen that the DVS 1100 is installed slightly below on an actual living room space since the vanishing point 301 exists slightly above the center of the image 300 of the living room.

According to an example embodiment, the fall detection device 1000 may perform image processing on an initial image to obtain information such as types of objects on the space in which the DVS 1100 is installed, positions, a percentage of obstacles, a percentage of a floor surface, etc.

In operation S250, the fall detection device 1000 may determine whether installation of the DVS 1100 is suitable based on the analyzed space information using the initial image.

For example, the fall detection device 1000 may determine that the installation of the DVS 1100 is unsuitable because it is difficult to detect a fall when the percentage of the floor surface in the initial image is less than or equal to a threshold value (for example, 10%). On the other hand, the fall detection device 1000 may determine that the installation of the DVS 1100 is suitable when the percentage of the floor surface in the initial image is greater than the threshold value (e.g., 10%).

Also, the fall detection device 1000 may determine that the installation of the DVS 1100 is unsuitable if a percentage of an area occupied by obstacles that do not move in the initial image is greater than a threshold value (e.g., 70%). The fall detection device 1000 may determine that the installation of the DVS 1100 is unsuitable when the number of times occlusions that an obstacle covers a moving object (e.g., a person) is greater than a threshold value. On the other hand, the fall detection device 1000 may determine that the installation of the DVS 1100 is suitable when the number of times occlusions that the obstacle covers the moving object (e.g., the person) is less than or equal to the threshold value.

According to an example embodiment, the fall detection device 1000 may score (e.g., 90 points, 40 points, good, bad, etc.) an installation position.

If it is determined in operation S260 that the installation of the DVS 1100 is suitable, the fall detection device 1000 may obtain an image through the DVS 1100 and monitor whether the object falls. A method in which the fall detection device 1000 determines whether the object falls will be described in detail later with reference to FIG. 7.

If it is determined in operation S270 that the installation of the DVS 1100 is unsuitable, the fall detection device 1000 may provide installation guide information. According to an example embodiment, the fall detection device 1000 may provide information indicating that the installation of the DVS 1100 is unsuitable, information requesting reinstallation of the DVS 1100, or information guiding an installation position of the DVS 1100 to a user.

The operation of the fall detection device 1000 providing the installation guide information will be described in further detail with reference to FIG. 4.

Figure 4:
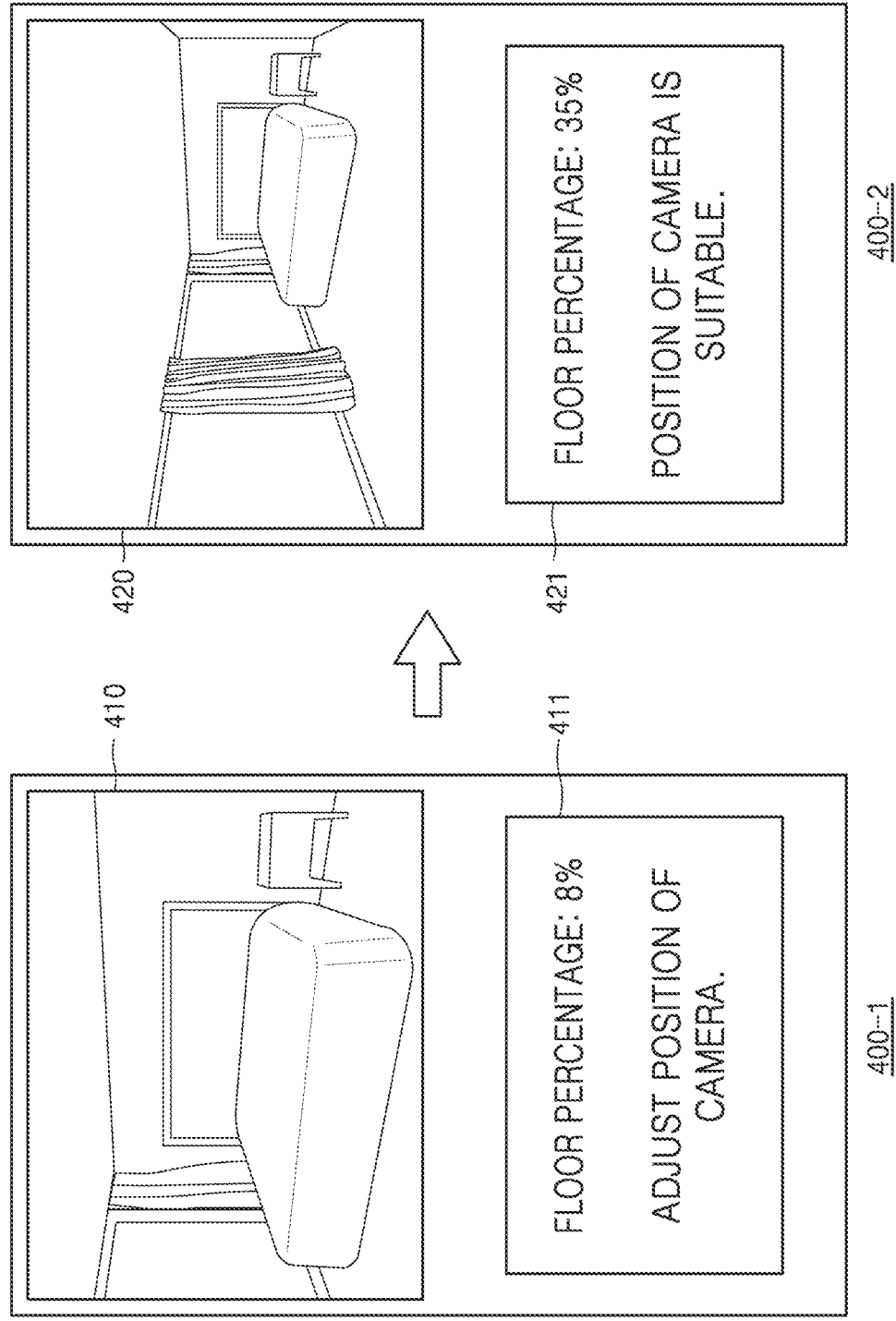
FIG. 4 is a diagram illustrating an operation of a fall detection device providing installation guide information, according to an example embodiment.

FIG. 4 is a diagram illustrating an operation of the fall detection device 1000 providing installation guide information according to an example embodiment.

Referring to 400-1 of FIG. 4, the fall detection device 1000 may move the DVS 1100 by using the vibrator 1200 upon booting, thereby obtaining an initial image 410 of a bedroom in which the DVS 1100 is installed. If a floor percentage (e.g., 8%) is less than or equal to a threshold value (e.g., 10%) as a result of analyzing the initial image 410 of the bedroom, the fall detection device 1000 may determine that an installation of the DVS 1100 is unsuitable for detecting a fall. The fall detection device 1000 may output a message 411 (e.g., floor percentage: 8%, Please adjust a position of a camera) inducing a position adjustment of the DVS 1100.

A user may adjust a pose of the DVS 1100 according to the message 411. For example, the user may adjust an installation angle of the DVS 1100, a direction in which the DVS 1100 looks, or an installation position of the DVS 1100 in order to increase the floor percentage recognized by the DVS 1100. When the user adjusts a position of the DVS 1100, the fall detection device 1000 may reboot.

Referring to 400-2 of FIG. 4, the fall detection device 1000 may move the DVS 1100 upon rebooting to obtain an initial image 420 of the bedroom in which the DVS 1100 is installed. If the floor percentage (e.g., 35%) is greater than a threshold value (e.g., 10%) as a result of analyzing the initial image 420 of the bedroom, the fall detection device 1000 may determine that the installation of the DVS 1100 is suitable for detecting the fall. The fall detection device 1000 may output a message 421 (e.g., floor percentage: 35%, The position of the camera is suitable) indicating that the installation of the DVS 1100 is suitable.

Figure 5:
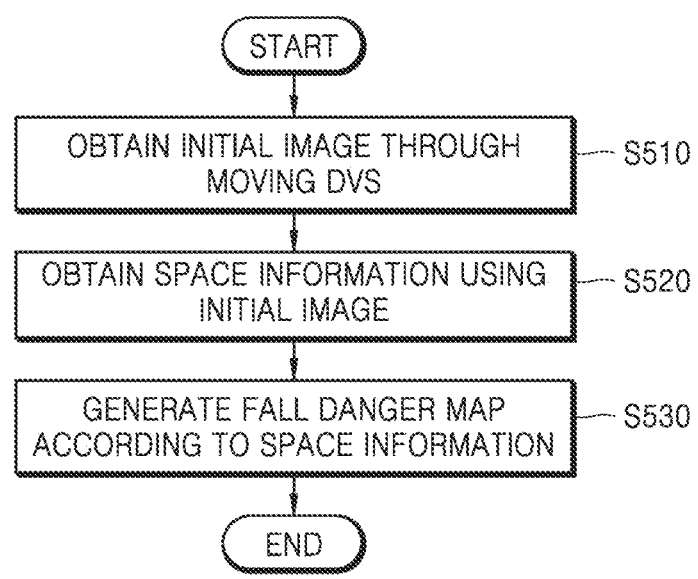
FIG. 5 is a flowchart of a method of generating a fall danger map, according to an example embodiment.

FIG. 5 is a flowchart illustrating a method of generating a fall danger map according to an example embodiment.

In operation S510, the fall detection device 1000 may obtain an initial image through the moving DVS 1100. For example, the fall detection device 1000 may move the DVS 1100 by outputting a vibration signal using the vibrator 1200 upon booting. At this time, the fall detection device 1000 may obtain an initial image of a space in which the DVS 1100 is installed through the moving DVS 1100. Operation S510 corresponds to operation S230 of FIG. 2, and thus a detailed description thereof will be omitted.

In operation S520, the fall detection device 1000 may obtain space information about the space where the DVS 1100 is installed, using the initial image obtained through the DVS 1100. For example, the fall detection device 1000 may obtain information about relative positions of objects using a vanishing point of the initial image. The fall detection device 1000 may perform image processing on the initial image to obtain information such as type and positions of objects present in the space in which the DVS 1100 is installed. For example, the fall detection device 1000 may detect an object type, an object name, and the like by comparing an outline of an object included in an image with a predefined template. Alternatively, the fall detection device 1000 may obtain information such as types, positions, and the like of the objects included in the initial image using deep learning algorithm.

In operation S530, the fall detection device 1000 may generate the fall danger map according to space information of the space where the DVS 1100 is installed. The fall danger map may be a map showing relatively more dangerous areas and less dangerous areas when a fall occurs.

According to an example embodiment, the fall detection device 1000 may generate the fall danger map using information about predefined fall danger weights. For example, a stairs region may have a fall danger weight of +2, a floor with a carpet may have a fall danger weight of −1, an edge of a table may have a fall danger weight of +3, and a bathroom floor may have a fall danger weight of +1.

According to an example embodiment, the fall detection device 1000 may generate a fall danger map in which a fall danger region is highlighted or displayed in a specific color, or a specific mark or text is added to the fall danger region. For example, the fall detection device 1000 may generate the fall danger map that displays the stairs region, the edge of the table, and the bathroom floor in a specific color (e.g., red). The fall danger map will be described in more detail with reference to FIG. 6.

Figure 6:
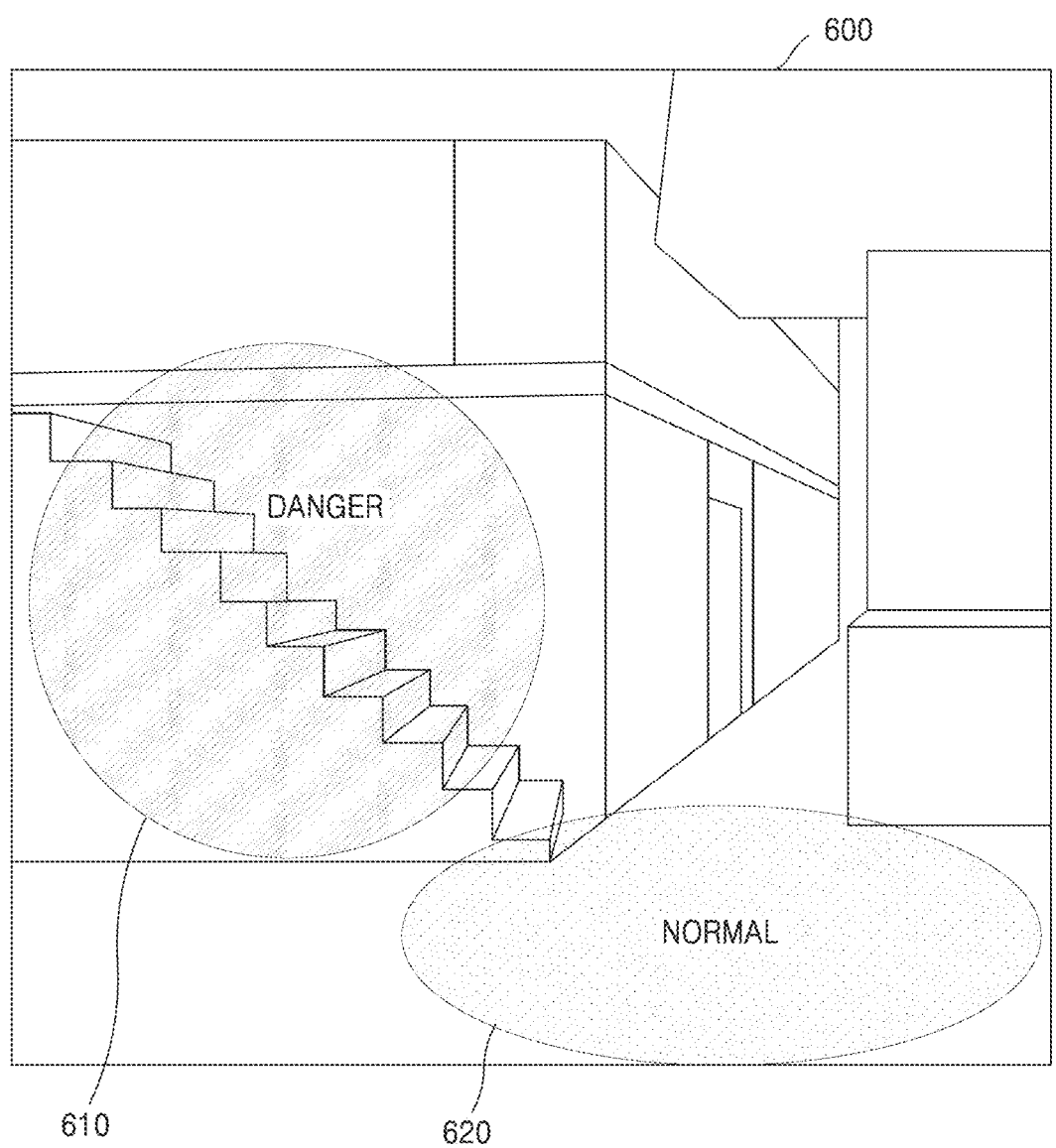
FIG. 6 is a diagram illustrating a fall danger map according to an example embodiment.

FIG. 6 is a diagram illustrating a fall danger map 600 according to an example embodiment.

Referring to FIG. 6, the fall detection device 1000 may generate the fall danger map 600 in which a danger level of a stairs region 610 is designated as 'danger' and a danger level of a living room floor 620 is designated as 'normal'.

According to an example embodiment, the fall detection device 1000 may quickly determine a danger associated with a fall, taking into account the fall danger map 600 when the fall occurs. For example, the fall detection device 1000 may raise a fall danger by two steps when the fall occurs in the stair region 610.

Hereinafter, a method in which the fall detection device 1000 detects a fall of an object using at least one image collected through the DVS 1100 will be described in detail with reference to FIG. 7.

FIG. 7 is a flowchart illustrating a method of detecting a fall according to an example embodiment.

In operation S710, the fall detection device 1000 may obtain at least one image including a movable first object, using the DVS 1100. According to an example embodiment, the movable first object may be a person who is a monitoring target. When the first object moves, the DVS 1100 may capture an image of the first object. The image of the first object may include an outline, an edge, and/or a silhouette of the first object.

In operation S720, the fall detection device 1000 may detect a first image including the first object in a predefined pose from the at least one image. At this time, each of the at least one image may be a static image.

According to an example embodiment, the fall detection device 1000 may analyze at least one image obtained through the DVS 1100 one by one using a first deep learning model. The first deep learning model may be a learned model for analyzing the static image and detecting an image including an object in a predefined pose.

The predefined pose may be a pose associated with the fall. According to an example embodiment, the predefined pose may be a pose in which a particular body part (e.g., head, back, chest, knee, heel, palm, etc.) is in contact with a floor (or stairs). For example, the predefined pose may be, but is not limited to, a pose lying with the back on the floor, a pose lying with the belly on the floor, a pose lying with one flank (e.g., side of body) on the floor, a pose leaning against the stairs, and the like.

For example, when a grandfather comes out of bed and falls, the fall detection device 1000 may analyze images one by one using the first deep learning model, and then detect an image including the grandfather in a pose lying on the floor.

Meanwhile, according to an example embodiment, the fall detection device 1000 may compensate for a body shape or a size of an object included in the static image before analyzing the static image using the first deep learning model. For example, the fall detection device 1000 may compensate for a body shape or a size of the first object included in the at least one image, taking into account at least one of the angle and the position at which the DVS 1100 is installed and compare a pose of the first object having the compensated body shape or size with the predefined pose. An operation of the fall detection device 1000 compensating for the body shape or size of the object will be described in detail later with reference to FIG. 9.

According to an example embodiment, the fall detection device 1000 may compensate for an occlusion before analyzing the static image using the first deep learning model. An operation of the fall detection device 1000 compensating for the occlusion will be described later in detail with reference to FIG. 12.

In operation S730, when a first image including the first object in the predefined pose is detected, the fall detection device 1000 may analyze a plurality of images with respect to the first object including the first image to obtain information about a first movement change of the first object. According to an example embodiment, the plurality of images may include at least one from among frames obtained earlier than the first image and frames obtained later than the first image using the DVS 1100 but are not limited thereto.

According to an example embodiment, when the first image including the first object in a pose associated with a fall is detected, the fall detection device 1000 may analyze a series of images (e.g., accumulated frames for a certain period of time) to obtain the information about the first movement change of the first object, in order to accurately determine whether a situation of the first object is a fall situation. For example, if an image (for example, an nth frame) in which the first object is lying on a floor apart from a bed is detected, the fall detection device 1000 may analyze images accumulated for a certain period of time (e.g., an (n−10)th frame~an (n+10)th frame) to detect a change in a movement of the first object falling from the bed to the floor. Also, the fall detection device 1000 may detect a change in the movement of the first object after the body touches the floor.

In operation S740, the fall detection device 1000 may determine whether the situation of the first object is the fall situation, based on the information about the first movement change of the first object.

According to an example embodiment, when a similarity between the first movement change of the first object and a second movement change representing a previously stored fall is greater than a threshold value (e.g., 90%), the fall detection device 1000 may determine that the situation of the first object is the fall situation. On the other hand, when the similarity between the first movement change of the first object and the second movement change representing the previously stored fall is less than or equal to the threshold value (for example, 90%), the fall detection device 1000 may determine that the situation of the first object is not the fall situation.

For example, when a movement change of the first object is similar to a movement pattern of the fall (e.g., when the first object is no longer movable after having fallen from the bed to the floor), the fall detection device 1000 may determine that the situation of the first object is the fall situation. However, when the movement change of the first object is different from the movement pattern of the fall (for example, when the first object slides down from the bed and the hips and the palm touch the floor but immediately stands up and walks), the fall detection device 1000 may determine that the situation of the first object is not the fall situation. A method in which the fall detection device 1000 detects a fall of an object will be described in more detail with reference to FIG. 8A.

Figure 8A:
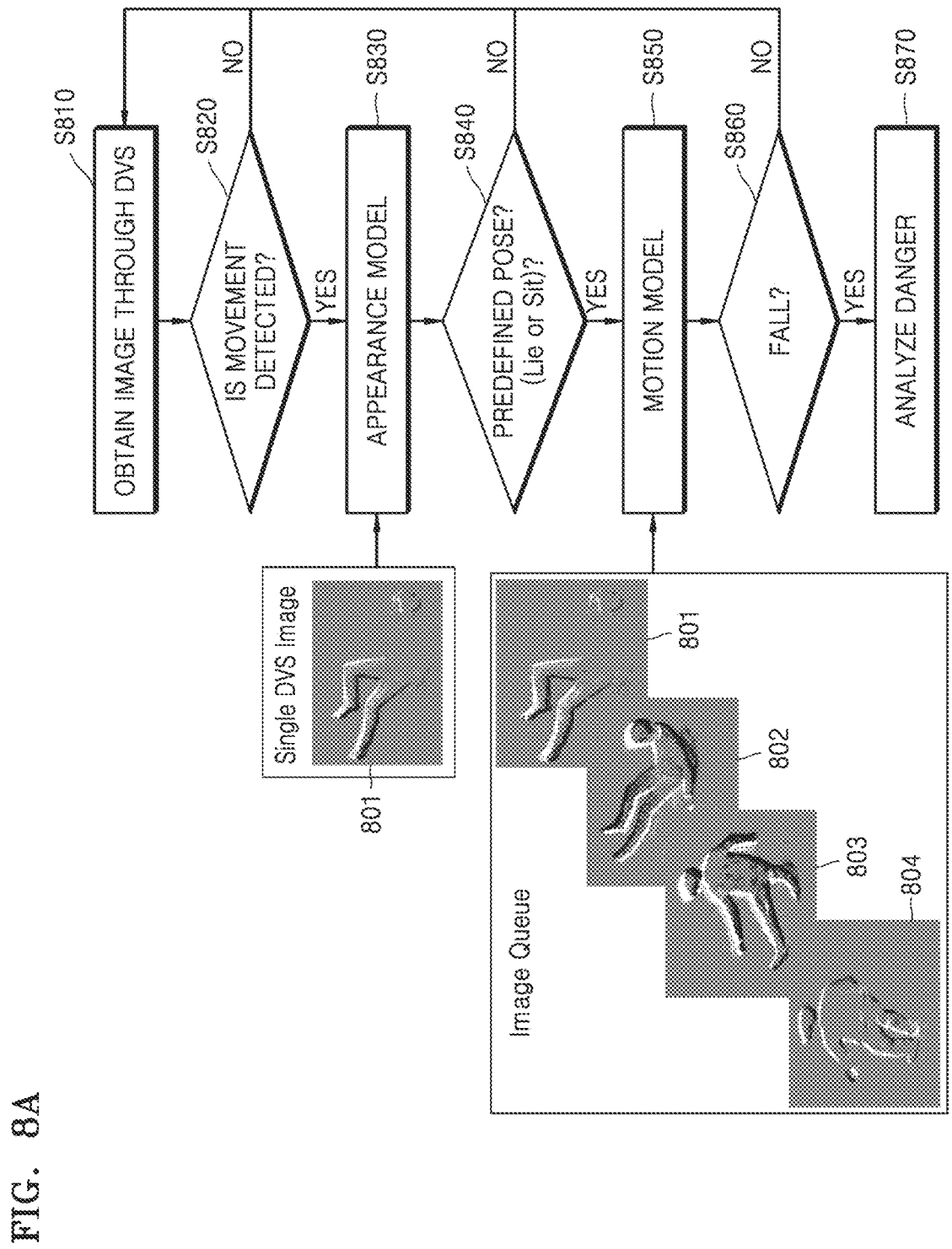
FIG. 8A is a flowchart of a method of detecting a fall by using an appearance model and a motion model, according to an example embodiment.

FIG. 8A is a flowchart illustrating a method of detecting a fall using an appearance model and a motion model according to an example embodiment.

In operation S810, the fall detection device 1000 may obtain at least one image through the DVS 1100. At this time, an outline of a moving object may appear on the at least one image, and an outline of a non-moving object may not appear. For example, if a first object is moving and second, third, and fourth objects are not moving, only an outline of the first object may appear on the at least one image.

In operation S820, the fall detection device 1000 may detect a movement of an object using the at least one image obtained through the DVS 1100.

For example, when a person is not present in a room with a bed and a dresser, no outline may appear in the at least one image obtained through the DVS 1100. However, when a person comes into the room with the bed and the dresser, an outline of the moving person appears on the at least one image obtained through the DVS 1100. Accordingly, the fall detection device 1000 may detect whether the object (e.g., a person) is moving by analyzing the at least one image.

If the movement of the object (e.g., the person) is not detected, since there is no likelihood of a fall, the fall detection device 1000 may no longer analyze an image obtained through the DVS 1100. If the movement of the object (e.g., the person) is detected, the fall detection device 1000 may perform operation S830 to determine if the movement of the object (e.g., the person) is a fall related movement.

In operation S830, when the movement of the object is detected, the fall detection device 1000 may analyze the at least one image obtained through the DVS 1100 one by one using the appearance model. For example, the fall detection device 1000 may use the appearance model to detect an image (e.g., an image including a person in a pose lying on a floor) including an object of a fall related pose. The appearance model may be a learned model to analyze static images one by one to detect a body shape or a pose of an object included in the static images and determine whether the detected shape or pose of the object is similar to the fall related pose.

For example, when a grandfather enters a bathroom where the DVS 1100 is installed, the DVS 1100 may detect a movement of the grandfather. The DVS 1100 may sequentially transfer image frames captured from a time when the movement of the grandfather is detected to a processor of the fall detection device 1000. The processor may analyze the sequentially transferred image frames using the appearance model. For example, the processor may detect poses of the grandfather included in the sequentially transferred image frames.

If the grandfather falls on a bathroom floor, the processor of the fall detection device 1000 may detect an nth frame 801 including the grandfather in a pose with his back not touching the bathroom floor among the sequentially transferred image frames.

In operation S840, the processor of the fall detection device 1000 may determine whether a pose of the object detected in the sequentially transferred image frames is similar to a predefined pose (e.g., a lying pose).

If the detected pose of the object is not similar to the predefined pose, the fall detection device 1000 may return to operation S810 to obtain a next image frame through the DVS 1100. On the other hand, if the detected object pose is similar to the predefined pose, the fall detection device 1000 may perform operation S850 to accurately determine whether the object falls.

For example, when a previous (n−3)th frame 804 is input, since a pose of the object included in the (n−3)th frame 804 is not the lying pose, the processor of the fall detection device 1000 may return to operation S810 to obtain an (n−2)th frame 803 through the DVS 1100. When the (n−2)th frame 803 is input, since a pose of the object included in the (n−2)th frame 803 is not the lying pose, the processor of the fall detection device 1000 may return to operation S810 to obtain an (n−1)th frame 802 through the DVS 1100. When the (n−1)th frame 802 is input, since a pose of the object included in the (n−1)th frame 802 is not the lying pose, the processor of the fall detection device 1000 may return to operation S810 to obtain an nth frame 801 through the DVS 1100.

When the nth frame 801 is input, since a pose of the object included in the nth frame 801 is the lying pose, the processor of the fall detection device 1000 may proceed to operation S850.

In operation S850, the fall detection device 1000 may detect a movement change using the motion model, and determine whether the detected movement change is similar to a movement change indicating a fall.

According to an example embodiment, the motion model may be a learned model to analyze a plurality of images (e.g., moving images) to detect a movement pattern of objects, and determine whether the detected movement pattern of the objects is similar to a movement pattern representing a fall.

According to an example embodiment, since the nth frame 801 including the object of the lying pose in operation S830 and operation S840 is detected, the fall detection device 1000 may analyze a series of images (e.g., the (n−3)th frame 804, the (n−2)th frame 803, the (n−1)th frame 802, and the nth frame 801) related to the nth frame 801 using the motion model.

The fall detection device 1000 may analyze the set of images (e.g., the (n−3)th frame 804, the (n−2)th frame 803, the (n−1)th frame 802, and the nth frame 801) to detect a movement pattern of a grandfather standing on the bathroom floor (e.g., the (n−3)th frame 804), sliding (e.g., the (n−2)th frame 803), his hips touching the floor (e.g., the (n−1)th frame 802), and then his back and head touching the bathroom floor (e.g., the nth frame 801). At this time, the fall detection device 1000 may determine that the detected movement pattern of the grandfather is similar to a movement pattern representing a previously learned fall.

In operation S860, if the detected movement change is not similar to the movement change indicating the fall, the fall detection device 1000 may return to operation S810 to obtain a next image through the DVS 1100. On the other hand, the fall detection device 1000 may determine the situation of the object as a fall situation when the detected movement change is similar to the movement change representing the fall.

In operation S870, the fall detection device 1000 may analyze a danger of the fall situation when the situation of the object is determined as the fall situation.

According to an example embodiment, the fall detection device 1000 may analyze the danger of the fall situation using information about which pose an object has fallen into, whether the object has continuous movement after having fallen or not, and the like. According to an example embodiment, the fall detection device 1000 may analyze the danger of the fall situation using information of a surrounding environment in which the object has fallen (for example, a subject present at which the object has fallen, a material of the floor, etc.) According to an example embodiment, the fall detection device 1000 may analyze the danger of the fall situation using the previously generated fall danger map 600. An operation of the fall detection device 1000 analyzing the danger of the fall situation will be described later in detail with reference to FIG. 14.

In general, the motion model stacks (for example, N images stacking) and processes multiple images, which takes N times longer than the appearance model that processes a single image. However, since the fall detection device 1000 according to an example embodiment operates the motion model only when the fall detection device 1000 recognizes a scene in which the body is closely attached to the floor using the appearance model, computation resources for fall detection may be efficiently used.

Figure 8B:
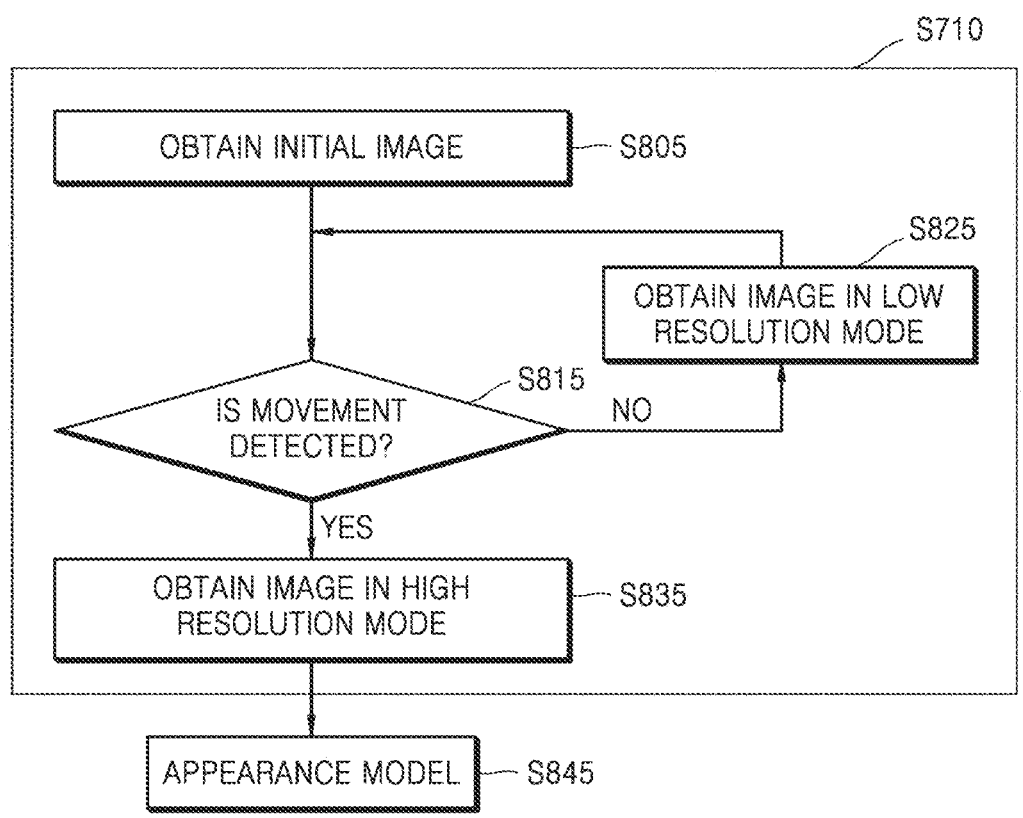
FIG. 8B is a flowchart of a method of adjusting an image acquisition mode, depending on whether a movement of an object is detected, according to an example embodiment.

FIG. 8B is a flowchart illustrating a method of adjusting an image acquisition mode depending on whether a movement of an object is detected according to an example embodiment.

In operation S805, the fall detection device 1000 may obtain an initial image using the DVS 1100.

According to an example embodiment, a resolution of the initial image may be changed according to a system setting value or a user setting value. For example, the initial image may be a high resolution image or a low resolution image. Here, the high resolution image may mean an image whose resolution is greater than a threshold value, and the low resolution image may mean an image whose resolution is smaller than or equal to the threshold value.

In operation S815, the fall detection device 1000 may detect a movement of an object using the initial image.

For example, if there is no person in a kitchen, the initial image obtained through the DVS 1100 may not show any outlines or edges at all. However, when a person enters the kitchen, an outline or edge of the moving person appears in the initial image obtained through the DVS 1100. Accordingly, the fall detection device 1000 may detect whether an object (e.g., the person) is moving by analyzing the initial image.

In operation S825, the fall detection device 1000 may obtain an image in a low resolution mode when the movement of the object is not detected. Here, the low resolution mode may mean a mode in which a low resolution image whose resolution is equal to or less than a threshold value is obtained by using the DVS 1100.

For example, if the outline or edge of the object is not detected in the initial image (an nth frame), the fall detection device 1000 may obtain an (n+1)th frame in the low resolution mode using the DVS 1100. If the outline or edge of the object is not detected even in the (n+1)th frame, the fall detection device 1000 may obtain an (n+2)th frame in the low resolution mode using the DVS 1100.

If the movement of the object is not detected, since a fall is unlikely to occur, the fall detection device 1000 may use the DVS 1100 to obtain the low resolution image, thereby saving computing resources.

In operation S835, the fall detection device 1000 may obtain an image in a high resolution mode when the movement of the object is detected. Here, the high resolution mode may mean a mode in which a high resolution image whose resolution is greater than a threshold value by using the DVS 1100. According to an example embodiment, the high resolution mode may be a full resolution mode.

For example, when the outline or edge of the object is detected in the initial image (the nth frame), the fall detection device 1000 may obtain the (n+1)th frame in the high resolution mode using the DVS 1100. When the outline or edge of the object is not detected in the initial image (the nth frame) whereas the outline or edge of the object is detected in the image (the (n+1)th frame) obtained in the low resolution mode, the fall detection device 1000 may obtain an (n+2)th frame in the high resolution mode using the DVS 1100.

In operation S845, the fall detection device 1000 may analyze the high resolution image obtained in the high resolution image mode using the appearance model. For example, the fall detection device 1000 may use the appearance model to detect a high resolution image (e.g., an (n+5)th frame including a person in a pose lying on a floor) including the object of a fall associated pose. In this case, the fall detection device 1000 may use the motion model to generate a series of images (e.g., an nth frame, an (n+1)th frame, an (n+2)th frame, an (n+3)th frame, an (n+4)th frame, and an (n+5)th frame) related to the (n+5)th frame. In this regard, the nth frame, the (n+1)th frame, the (n+2)th frame, the (n+3)th frame, the (n+4)th frame, and the (n+5)th frame may all be high resolution images obtained in the high resolution mode.

The fall detection device 1000 may detect a movement change of the object based on an analysis result and determine whether the detected movement change is similar to a movement change indicating the fall. The fall detection device 1000 may determine a situation of the object as a fall situation when the detected movement change is similar to the movement change indicating the fall. When the situation of the object is determined to be the fall situation, the fall detection device 1000 may analyze a danger of the fall situation.

Since operation S845 corresponds to operation S830 of FIG. 8A, a detailed description thereof is omitted.

Figure 9:
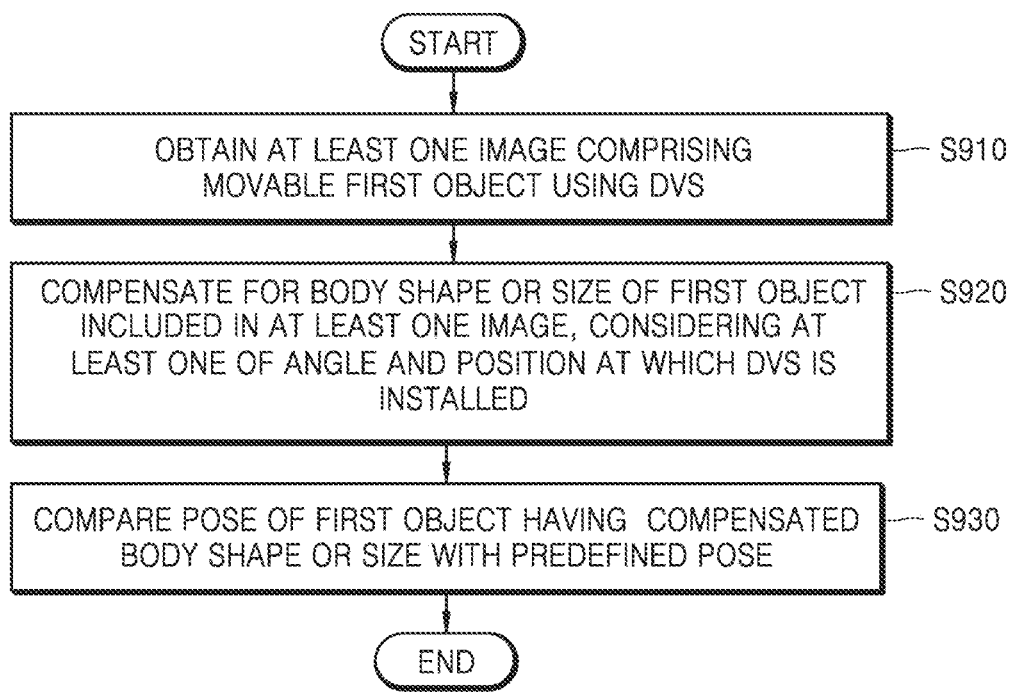
FIG. 9 is a flowchart of a method of compensating for a body shape or a size of an object, according to an example embodiment.

FIG. 9 is a flowchart illustrating a method of compensating for a body shape or a size of an object according to an example embodiment.

In operation S910, the fall detection device 1000 may obtain at least one image including a movable first object, using the DVS 1100. Operation S910 corresponds to operation S710 of FIG. 7, and thus a detailed description thereof is omitted.

In operation S920, the fall detection device 1000 may compensate for a body shape or a size of a first object included in the at least one image, considering at least one of an angle and a position at which the DVS 1100 is installed.

According to an example embodiment, as shown in FIG. 2, the fall detection device 1000 may analyze an initial image upon booting to obtain information about an angle, a position, and the like where a first DVS is installed. For example, the fall detection device 1000 may analyze a vanishing point of the initial image to verify the angle, the position, and a height where the first DVS is installed, a recognition range of the first dynamic vision sensor, and the like. In this case, the fall detection device 1000 may compare an installation angle, position or height of a second DVS used when generating an appearance model with the installation angle, position, or height of the first DVS installed in an actual space. If the installation angle, position, or height of the second DVS used to generate the appearance model and the installation angle, position, or height of the first DVS installed in the actual space are significantly different, an error in data recognition may increase. Accordingly, the fall detection device 1000 may compensate for the body shape of the object included in an image obtained through the first DVS, before operating the appearance model. An example of compensating for the body shape of the object will be further described with reference to FIG. 10.

Figure 10:
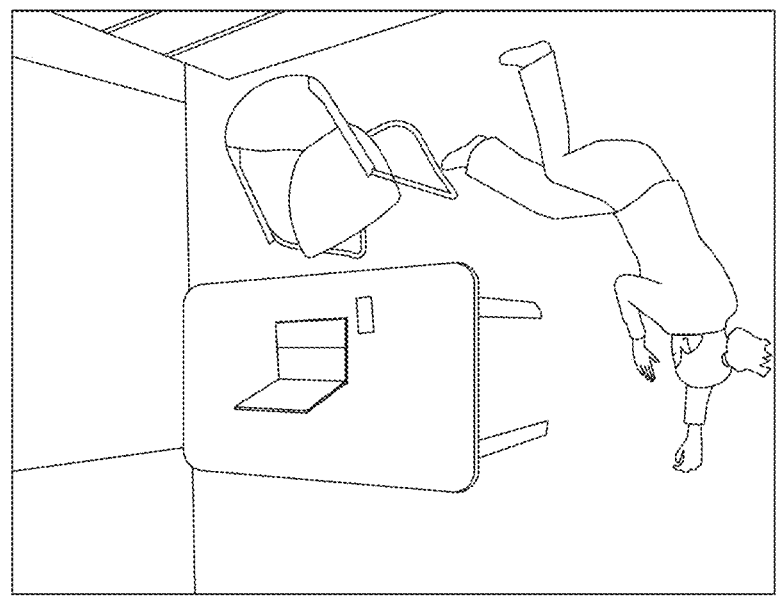
FIG. 10 is a diagram illustrating an operation of compensating for a body shape of an object considering an installation angle of a dynamic vision sensor (DVS), according to an example embodiment.

Referring to FIG. 10, although a second DVS 1100-2 used for generating an appearance model is placed on a tripod, a first DVS 1100-1 installed in an actual space may be located on a ceiling. In this case, when the fall detection device 1000 inputs an image obtained by using the first DVS 1100-1 to the appearance model, the appearance model may be difficult to accurately determine whether a pose of the object is similar to a previously learned fall pose. Therefore, the fall detection device 1000 may compensate for a body shape of a person included in a first image 1001 obtained by using the first DVS 1100-1 installed on the ceiling to the body shape as in a second image 1002.

Figure 11:
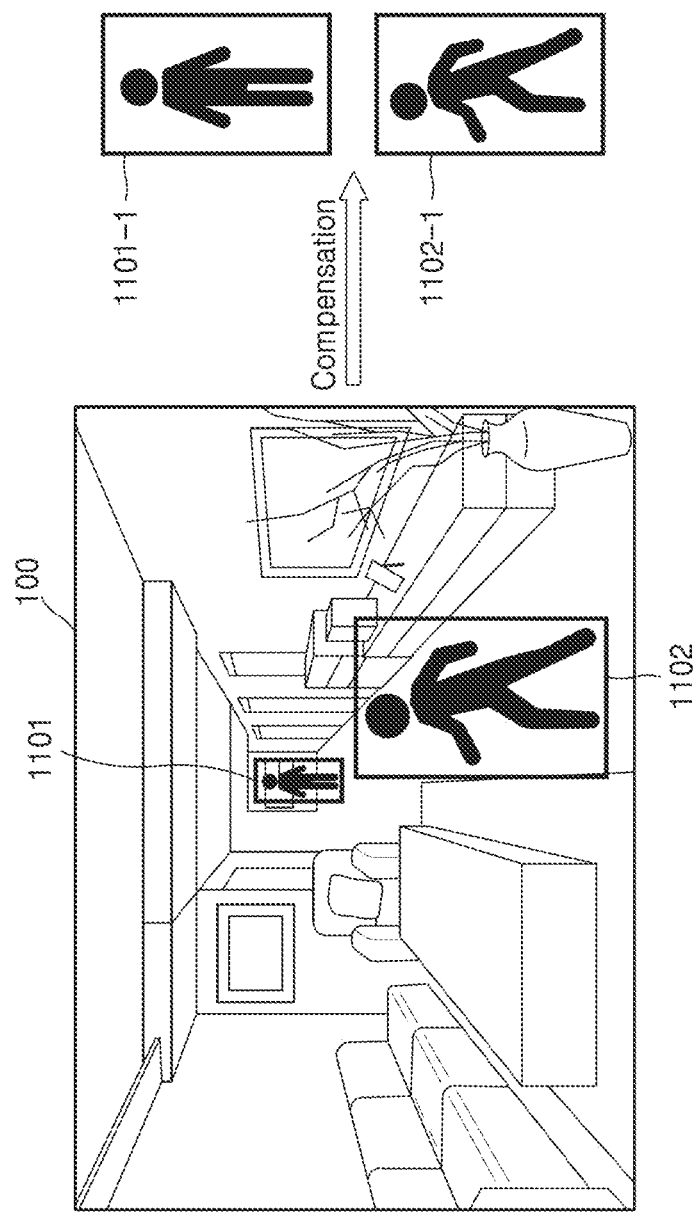
FIG. 11 is a diagram illustrating an operation of compensating for a size of an object by using vanishing point analysis, according to an example embodiment.

According to an example embodiment, the fall detection device 1000 may compensate for the size of the first object included in the at least one image 100, using the vanishing point of the at least one image. For example, referring to FIG. 11, although the first object 1101 and the second object 1102 have substantially the same size, the first object 1101 closer to the vanishing point appears smaller, and the second object 1102 farther from the vanishing point appears larger. Therefore, the fall detection device 1000 may compensate for the size of the first object 1101 close to the vanishing point to be large (1101-1). On the other hand, the fall detection device 1000 may compensate for the size of the second object 1102 far from the vanishing point to be small (1102-1).

In operation S930, the fall detection device 1000 may compare the pose of the first object having the compensated body shape or size with a predefined pose. The predefined pose may be a fall associated pose. For example, the predefined pose may be a pose in which a part of a person's body (e.g., a belly, a back, a flank, a head, etc.) touches the ground (e.g., a back lying pose, a belly lying pose, etc.). Operation S930 corresponds to operation S840 in FIG. 8A, and thus, a detailed description thereof will be omitted.

Figure 12:
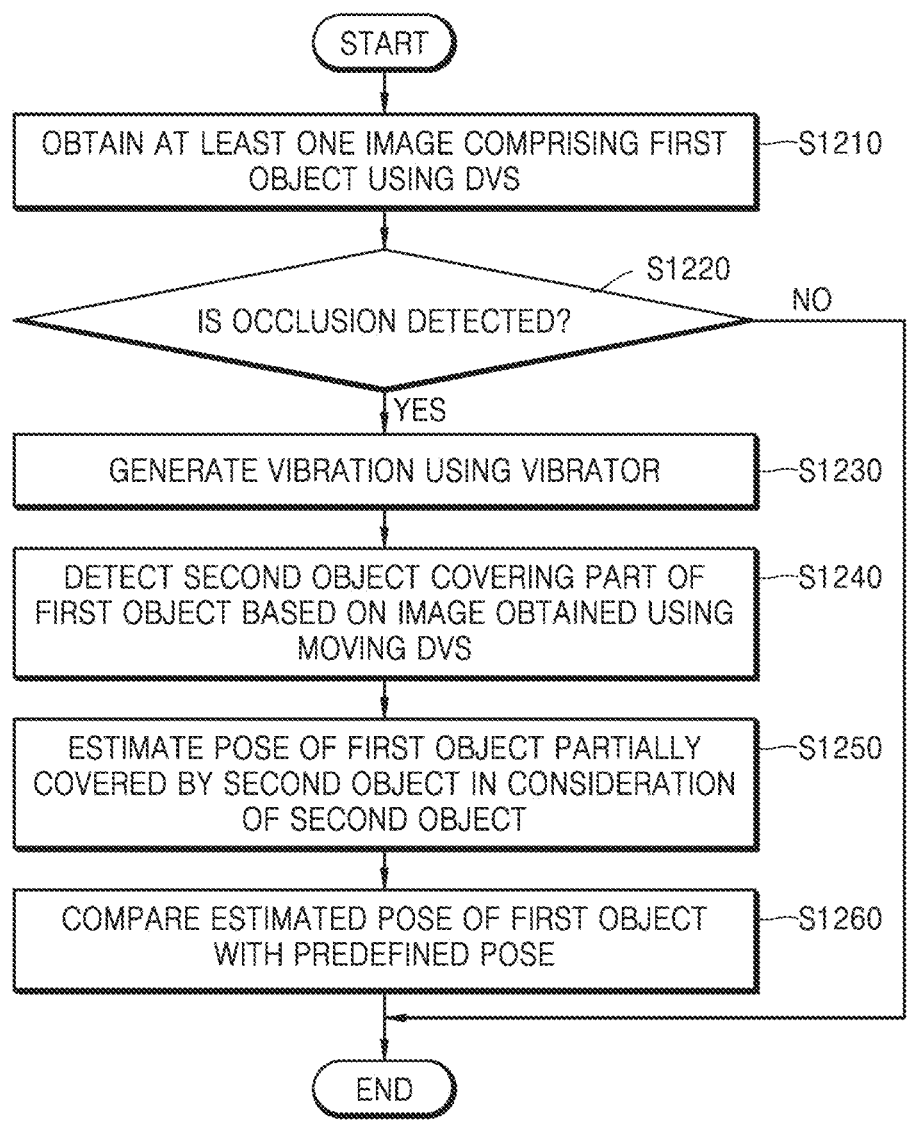
FIG. 12 is a flowchart of a method of estimating a pose of a first object partially covered by a second object, according to an example embodiment.

FIG. 12 is a flowchart illustrating a method of estimating a pose of a first object partially covered by a second object according to an example embodiment.

In operation S1210, the fall detection device 1000 may obtain at least one image including the first object, using the DVS 1100. Operation S1210 corresponds to operation S710 of FIG. 7, a detailed description thereof will be omitted.

In operation S1220, the fall detection device 1000 may detect occurrence of an occlusion using the at least one image. Occlusion may mean a phenomenon in which a moving object (e.g., a person) is partially or wholly covered by another object (e.g., an obstacle).

For example, when a whole body shape of a person is not detected in the at least one image and a partial body shape (e.g., a head, an upper body, etc.) of the person is detected, the fall detection device 1000 may determine that the occlusion has occurred.

In operation S1230, the fall detection device 1000 may generate vibration using a vibrator 1200 when the occlusion is detected. At this time, the vibration generated in the vibrator 1200 may move the DVS 1100.

In operation S1240, the fall detection device 1000 may detect a second object covering a part of the first object, based on the image obtained using the moving DVS 1100. When the DVS 1100 moves, since relative movements occurs with respect to objects, an image of the objects may be captured regardless of whether the objects are moving. Thus, the fall detection device 1000 may identify the second object (e.g., a bookcase, a sofa, a bed, etc.) that does not move covering the first object (e.g., a person).

In operation S1250, the fall detection device 1000 may estimate a pose of the first object partially covered by the second object, in consideration of the second object.

According to an example embodiment, the fall detection device 1000 may generate virtual data with respect to a part of the entire shape of the first object covered by the second object, using a learning model. The fall detection device 1000 may estimate the pose of the first object using the virtual data.

In operation S1260, the fall detection device 1000 may compare the estimated pose of the first object with a predefined pose. The predefined pose may be a fall associated pose. For example, the predefined pose may be a pose in which a part of a person's body (e.g., a belly, a back, a flank, a head, etc.) touches the ground (e.g., a back lying pose, a belly lying pose, etc.) but is not limited thereto. Operation S1260 corresponds to operation S840 in FIG. 8A, and thus a detailed description thereof will be omitted.

Hereinafter, an operation of the fall detection device 1000 compensating for the occlusion will be described in more detail with reference to FIG. 13.

Figure 13:
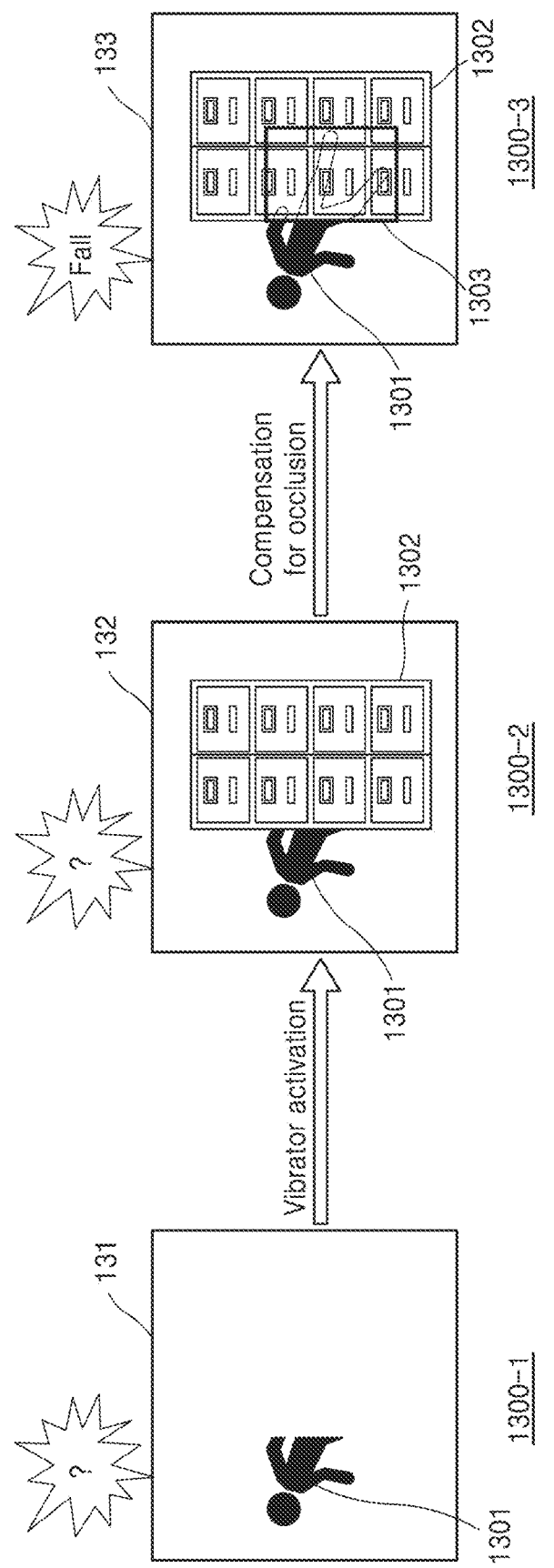
FIG. 13 is a diagram illustrating an operation of estimating a pose of an object when an occlusion is detected, according to an example embodiment.

FIG. 13 is a diagram illustrating an operation of estimating a pose of an object when an occlusion is detected according to an example embodiment. In FIG. 13, the case where a person 1301 falls behind a drawer 1302 will be described as an example.

Referring to 1300-1 in FIG. 13, when the person 1301 falls, since a movement occurs, the DVS 1100 may obtain an image 131 including the person 1301. At this time, the DVS 1100 may detect only a movement of an upper body part not covered by the drawer 1302, and may not detect a movement of a lower body part covered by the drawer 1302. Therefore, the lower body of the person 1301 does not appear in the image 131, and only the upper body of the person 1301 may appear.

In general, since there is no case where the upper body moves when a person falls, the fall detection device 1000 may detect the occlusion. That is, the fall detection device 1000 may determine that a part of the person 1301 is covered by an obstacle.

Referring to 1300-2 in FIG. 13, the fall detection device 1000 may output a vibration signal using the vibrator 1200, thereby making the DVS 1100 move. When the DVS 1100 moves, the DVS 1100 may detect the drawer 1302 as well. Thus, the DVS 1100 that moves may obtain an image 132 including the person 1301 and the drawer 1302.

Referring to 1300-3 in FIG. 13, the fall detection device 1000 may generate virtual data 1303 with respect to a lower body of the person 1301 covered by the drawer 1302. The fall detection device 1000 may estimate a pose of the person 1301 in an image 133 using the virtual data 1303 and determine whether the estimated pose is a predefined pose related to a fall.

Figure 14:
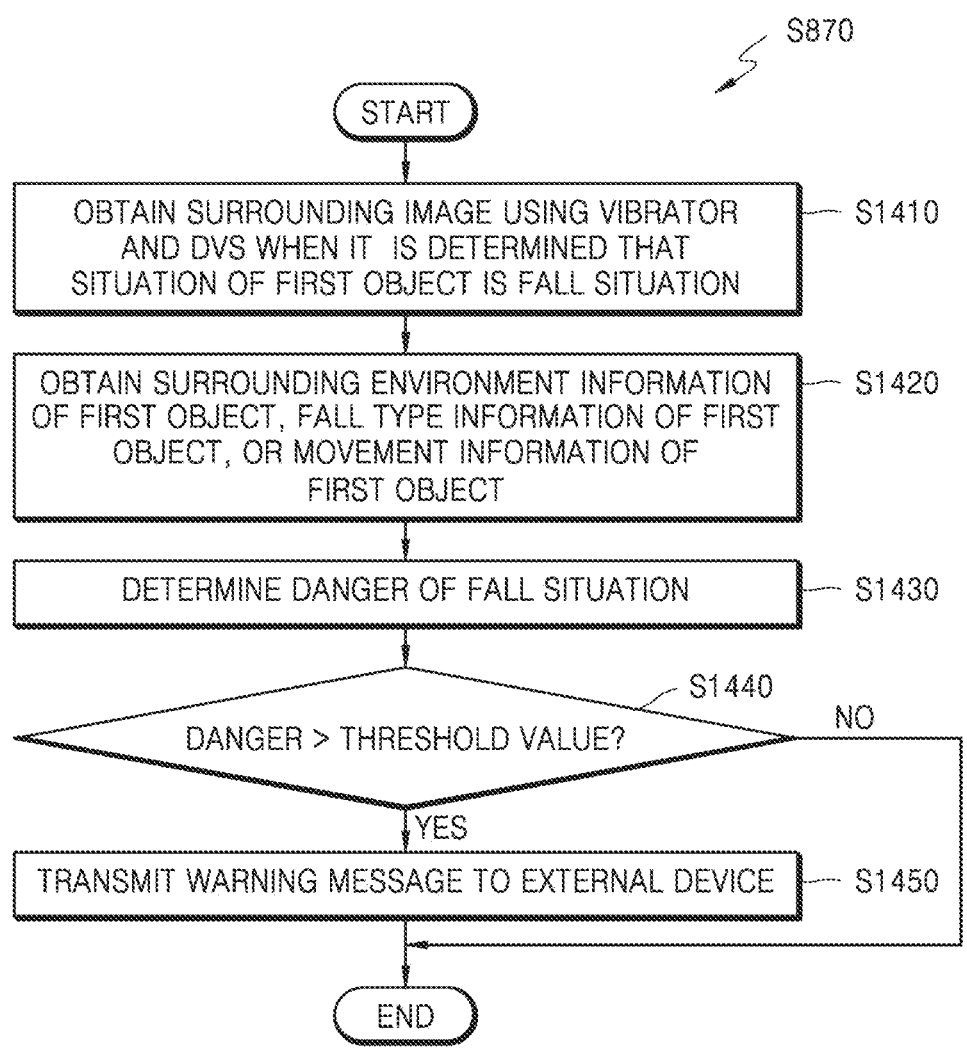
FIG. 14 is a flowchart of a method of determining a risk of a fall situation, according to an example embodiment.

FIG. 14 is a flowchart illustrating a method of determining a danger of a fall situation according to an example embodiment.

In operation S1410, the fall detection device 1000 may obtain a surrounding image using the vibrator 1200 and the DVS 1100 when a situation of a first object is determined as the fall situation. According to an example embodiment, when it is determined that the first object has fallen, the fall detection device 1000 may move the DVS 1100 using the vibrator 1200. At this time, the moving DVS 1100 may obtain a surrounding image including non-moving objects (e.g., a chair, a bed, a drawer, a sink, etc.) around the first object.

In operation S1420, the fall detection device 1000 may obtain surrounding environment information of the first object, fall type information of the first object, or movement information of the first object using the surrounding image.

According to an example embodiment, the surrounding environment information of the first object may include information (e.g., information about a dangerous object present at a place where a user falls, information about a thing fallen with the user, etc.), information about a material of a floor where the first object has fallen, information about whether the place where the first object has fallen is related to water, and the like, but is not limited thereto.

According to an example embodiment, the fall type information of the first object may be information about a pose indicating that the first object has fallen. For example, the fall type information of the first object may include, but is not limited to, information about whether the head or a face has touched the floor, information about whether an arm or a leg is broken, and the like.

The movement information of the first object may be information about a movement of the first object after the situation of the first object is determined as the fall situation. For example, the movement information of the first object may include a movement change value, total time information indicating that the movement change value is maintained below a threshold value, and the like, but is not limited thereto.

In operation S1430, the fall detection device 1000 may use the information obtained from the surrounding image to determine the danger of the fall situation. The danger of the fall situation may mean a degree of danger of an object with a fall.

According to an example embodiment, the fall detection device 1000 may determine the danger of the fall situation using the surrounding environment information of the first object. For example, if a protrusion exists at which the first object has fallen, the fall detection device 1000 may determine the danger of the fall situation to a high degree or raise a danger level. Also, when the material of the floor of the place where the first object has fallen is a slippery material with water, the fall detection device 1000 may determine the danger of the fall situation to a high degree or raise the danger level.

According to an example embodiment, the fall detection device 1000 may compare the surrounding environment information of the first object with the previously generated fall danger map 600 to determine the danger of the fall situation. For example, referring to FIG. 6, when the first object falls in the stairs region 610 designated as 'danger' in the previously generated fall danger map 600, the fall detection device 1000 may determine the danger of the fall situation to a high degree.

According to an example embodiment, the fall detection device 1000 may determine the danger of the fall situation using the fall type information of the first object. For example, when the first object touches the floor from the head when falls, the fall detection device 1000 may determine the danger of the fall situation to a high degree. Alternatively, if the leg is warped when the first object falls, the fall detection device 1000 may determine the danger of the fall situation to a high degree.

According to an example embodiment, the fall detection device 1000 may determine the danger of the fall situation using the movement information of the first object. According to an example embodiment, if the movement of the first object is smaller than a threshold value for a predetermined time, the fall detection device 1000 may raise the danger level of the fall situation. For example, if there is little movement for more than five minutes after the first object is determined to have fallen, the fall detection device 1000 may raise the danger of the fall situation by three steps.

According to an example embodiment, the fall detection device 1000 may combine at least two pieces of information among the surrounding environment information of the first object, the fall type information of the first object, and the movement information of the first object to determine the danger of the fall situation.

Meanwhile, according to an example embodiment, the fall detection device 1000 may determine the danger of the fall situation in consideration of personal information (e.g., age, physical activity ability, disease, etc.) of the first object. For example, if the first object is a healthy student of 10 years old, the fall detection device 1000 may determine a danger weight of the falling situation as −3. On the other hand, if the first object is an elderly man who is uncomfortable and has high blood pressure and is 80 years old, the fall detection device 1000 may determine the danger weight of the fall situation as '+5'.

In operations S1440 and S1450, the fall detection device 1000 may transmit a warning message to an external device when the danger of the fall situation is greater than the threshold value.

For example, the fall detection device 1000 may transmit a warning message (e.g., a first user has fallen from stairs and cannot move for two minutes) including information that the first object has fallen, surrounding environment information of the first object, time information that the movement of the first object is maintained below a threshold value to a predetermined external device (e.g., a family device, a medical institution server, an emergency rescue request server, etc.)

Hereinafter, an operation of the fall detection device 1000 determining the danger of the fall situation will be described in more detail with reference to FIG. 15.

Figure 15:
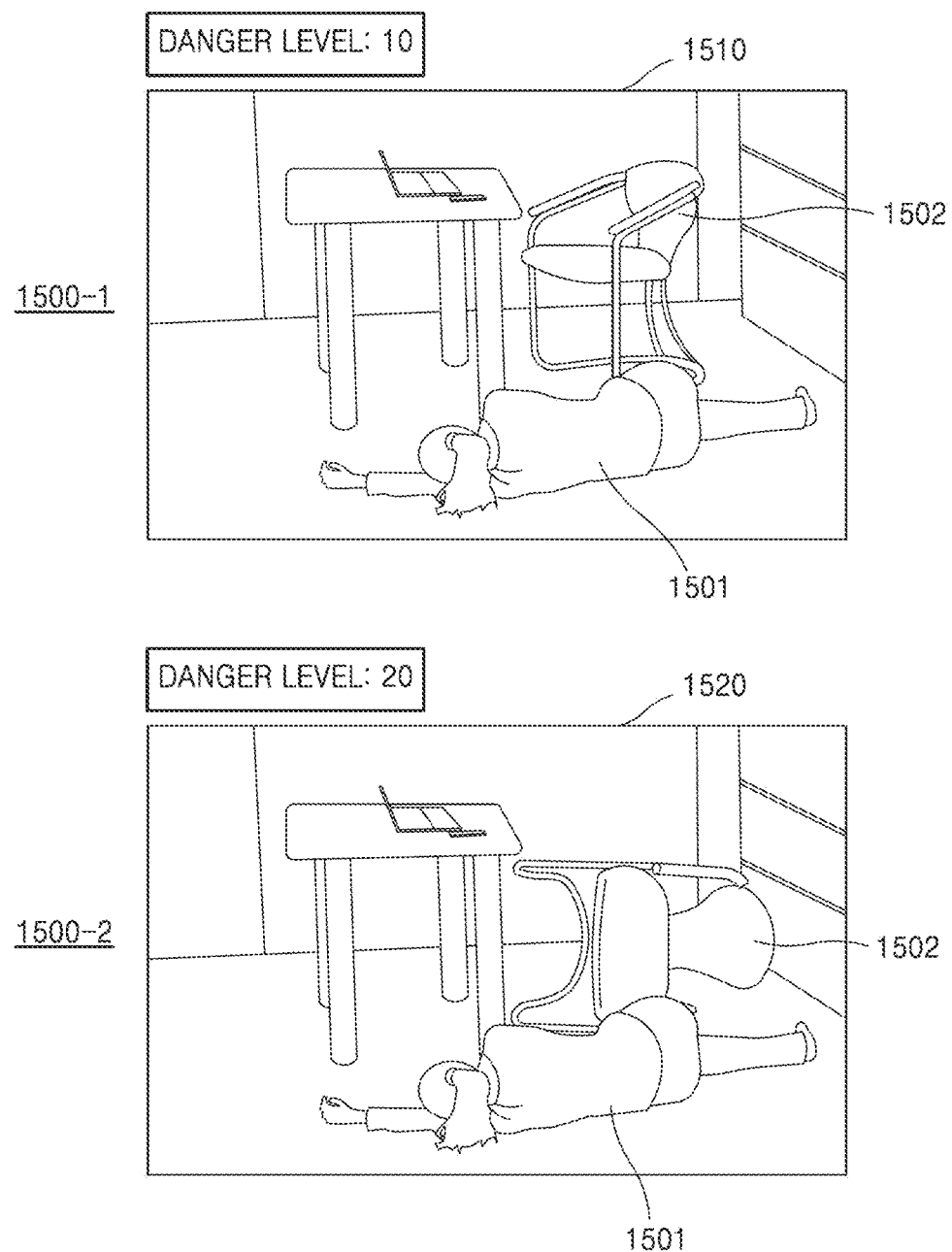
FIG. 15 is a diagram illustrating an operation of determining a danger level, according to an example embodiment.

FIG. 15 is a diagram illustrating an operation of determining a danger level according to an example embodiment. In FIG. 15, a case where a first user 1501 has fallen in an office will be described as an example.

Referring to 1500-1 of FIG. 15, the fall detection device 1000 may determine that the first user 1501 has fallen by using an appearance model and a motion model. At this time, the fall detection device 1000 may move the DVS 1100 using the vibrator 1200. The fall detection device 1000 may analyze at least one first image 1510 obtained through the moving DVS 1100. The fall detection device 1000 may analyze the at least one first image 1510 and determine that the first user 1501 does not move, a floor on which the first user 1501 has fallen is a material of a general floor paper, the first user 1501 puts on his/her shoes, the first user 1501 is more than 1 m away from a desk, and the desk and a chair 1502 do not fall. The fall detection device 1000 may use the information obtained as a result of analyzing the at least one image 1510 as a whole to determine a danger level of the fall situation as '10'.

Referring to 1500-2 in FIG. 15, the fall detection device 1000 may determine that the first user 1501 has fallen by using the appearance model and the motion model. At this time, the fall detection device 1000 may move the DVS 1100 using the vibrator 1200. The fall detection device 1000 may analyze at least one second image 1520 obtained through the moving DVS 1100.

The chair 1502 may be collapsed in the second image 1520 compared to the first image 1501. The fall detection device 1000 may determine that the situation of the first user 1501 is more dangerous when the chair 1502 falls with the first user 1501 compared to when only the first user 1501 falls. Accordingly, the fall detection device 1000 may determine the danger level of the falling situation as '20'.

Meanwhile, according to an example embodiment, the fall detection device 1000 may further determine the danger of the fall situation by further considering biometric information of a fallen object. An operation of the fall detection device 1000 determining the danger of the fall situation in consideration of the biometric information of the object will be described in detail with reference to FIG. 16.

Figure 16:
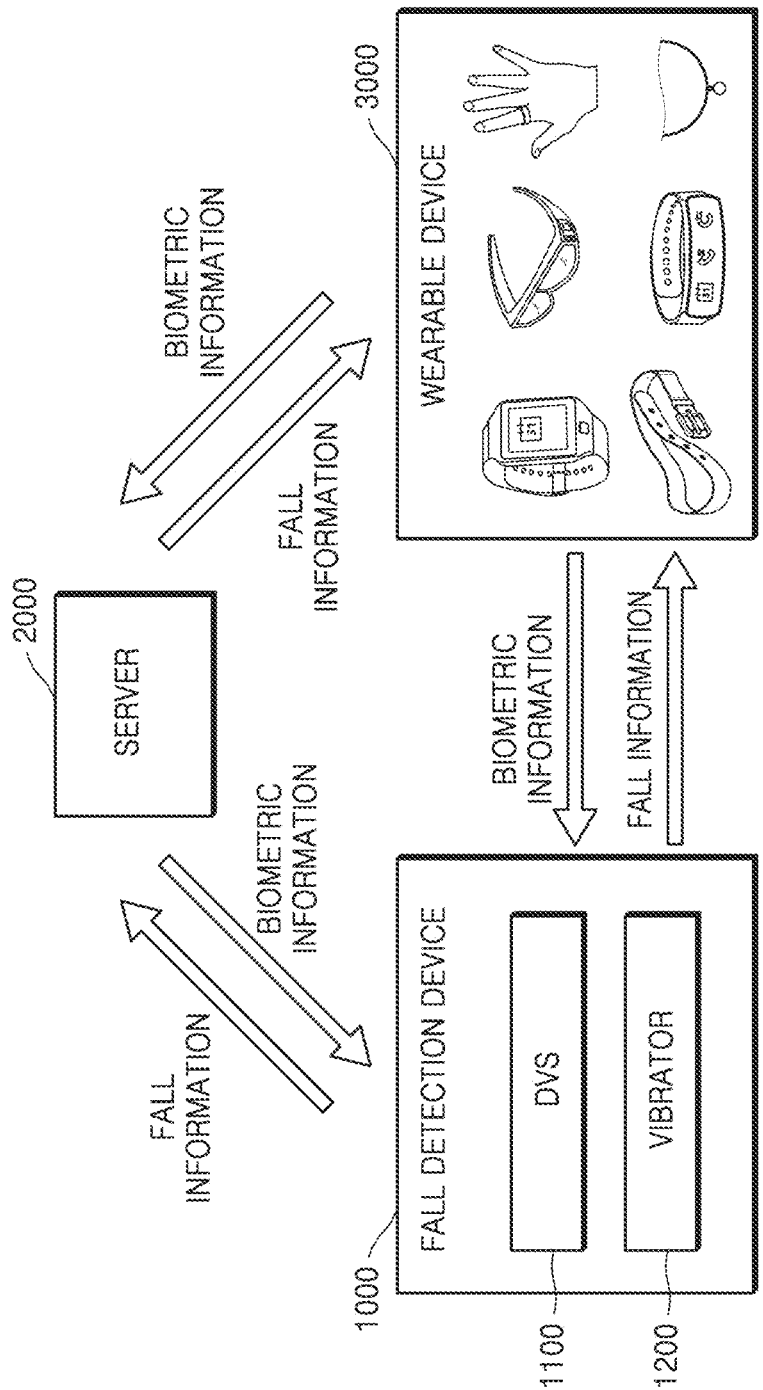
FIG. 16 is a diagram illustrating a system for analyzing a risk of a fall situation by using biometric information measured in a wearable device, according to an example embodiment.

FIG. 16 is a diagram illustrating a system for analyzing a danger of a fall situation using biometric information measured in a wearable device 3000 according to an example embodiment.

The system for analyzing the danger of the fall situation may include, but is not limited to, the fall detection device 1000, a server 2000, and the wearable device 3000. When the fall detection device 1000 is in direct communication with the wearable device 3000, the system for analyzing the danger of falling situation may not include the server 2000.

The wearable device 3000 may include at least one of an accessory-type device (e.g., a watch, a ring, a bracelet, an ankle, a necklace, and a contact lens), a head-mounted device (HMD), a fabric or clothing integrated device (e.g., electronic apparel), a body attachment device (e.g., a skin pad), and a bioimplantable device (e.g., an implantable circuit) but is not limited thereto.

According to an example embodiment, when a situation of a first object is determined as the fall situation, the fall detection device 1000 may obtain biometric information of the first object measured in the wearable device 3000 worn by the first object. At this time, the fall detection device 1000 may receive the biometric information directly from the wearable device 3000 or may receive the biometric information through the server 2000.

According to an example embodiment, the fall detection device 1000 may determine the danger of the fall situation in consideration of the biometric information of the first object. For example, if a heart rate is smaller than a threshold value, a blood pressure is equal to or greater than a threshold value, the number of breaths is smaller than a threshold value, a body temperature exceeds a threshold rage, or a current time is night, the fall detection device 1000 may determine the danger of the fall situation to a high degree.

According to an example embodiment, the server 2000 may receive fall information that the situation of the first object is the fall situation from the fall detection device 1000, and receive biometric information (e.g., blood pressure information, blood sugar information, heart rate information, body temperature information, etc.) of the first object from the wearable device 3000. In this case, the server 2000 may determine the danger of the fall situation of the first object using the fall information and the biometric information. If the danger of the fall situation is greater than the threshold value, the server 2000 may send a warning message to an external device (e.g., a healthcare institution server). According to an example embodiment, the server 2000 may transmit information about the danger of the fall situation to the fall detection device 1000 or the wearable device 3000.

According to an example embodiment, the wearable device 3000 may receive fall information that the situation of the first object is the fall situation from the fall detection device 1000 or the server 2000. At this time, the wearable device 3000 may determine the danger of the fall situation of the first object by using the biometric information of the first object measured by the wearable device 3000. If the danger of the fall situation is greater than the threshold value, the wearable device 3000 may send a warning message to an external device (e.g., a healthcare institution server). Also, according to an example embodiment, the wearable device 3000 may send information about the danger of the fall situation to the fall detection device 1000 or the server 2000.

Figure 17:
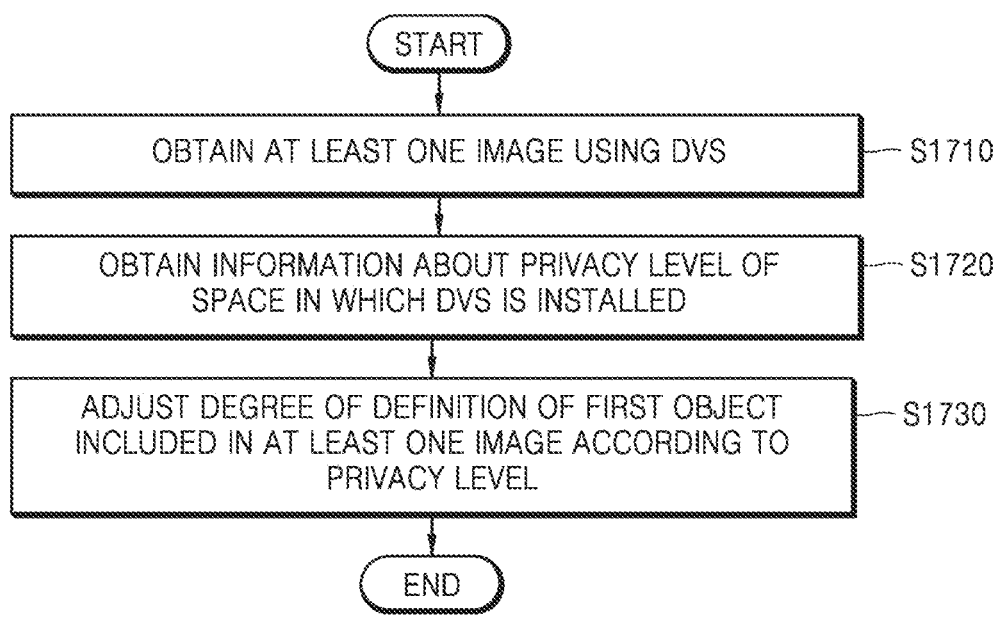
FIG. 17 is a flowchart of a method of adjusting a degree of definition of an object depending on a privacy level, according to an example embodiment.

FIG. 17 is a flowchart illustrating a method of adjusting a degree of definition of an object depending on a privacy level according to an example embodiment.

In operation S1710, the fall detection device 1000 may obtain at least one image using the DVS 1100. Operation S1710 corresponds to operation S710 of FIG. 7, and thus a detailed description thereof will be omitted.

In operation S1720, the fall detection device 1000 may obtain information about the privacy level of a space where the DVS 1100 is installed.

According to an example embodiment, the fall detection device 1000 may receive the privacy level from a user when the DVS 1100 is installed. According to an example embodiment, the fall detection device 1000 may obtain information about a predefined privacy level from the server 2000.

For example, privacy levels may be set very high for bathrooms or restrooms, relatively high for dress rooms or bedrooms, and relatively low for living rooms, kitchens, or staircases.

In operation S1730, the fall detection device 1000 may adjust the degree of definition of a first object included in the at least one image according to the privacy level. For example, the higher the privacy level of the space in which the at least one image is obtained, the lower the degree of definition of the first object may be adjusted. On the other hand, the lower the privacy level of the space in which the at least one image is obtained, the higher the degree of definition of the first object may be adjusted.

An operation of the fall detection device 1000 adjusting the degree of definition of the first object will be described in more detail with reference to FIG. 18.

Figure 18:
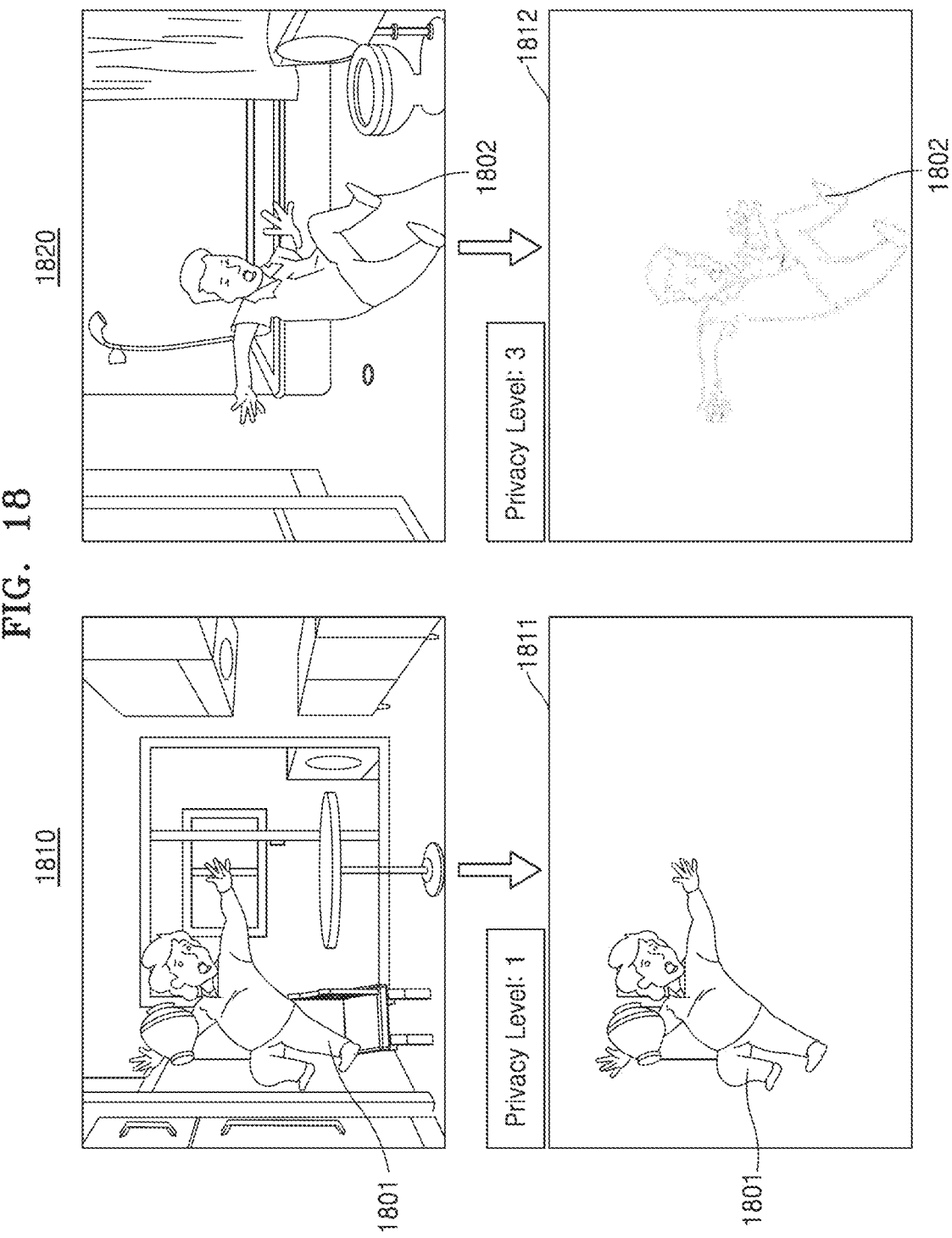
FIG. 18 is a diagram illustrating an operation of adjusting a degree of definition of an object, depending on a privacy level, according to an example embodiment.

FIG. 18 is a diagram illustrating an operation of adjusting a degree of definition of an object depending on a privacy level according to an example embodiment.

Referring to 1810 of FIG. 18, the first user 1801 may fall in a kitchen. At this time, the fall detection device 1000 may obtain an image 1811 of a first user 1801 that falls using the DVS 1100. The fall detection device 1000 may confirm a privacy level of the kitchen where the first user 1801 is located and express an outline of the first user 1801 with a degree of definition corresponding to the confirmed privacy level. For example, since the privacy level of the kitchen is a general level '1', the fall detection device 1000 may express the outline of the first user 1801 with a general degree of definition.

Referring to 1820 of FIG. 18, a second user 1802 may fall in a restroom. At this time, the fall detection device 1000 may obtain an image 1812 of a second user 1802 that falls using the DVS 1100. The fall detection device 1000 may confirm a privacy level of the restroom where the second user 1802 is located and express an outline of the second user 1802 with a degree of definition corresponding to the confirmed privacy level. For example, since the privacy level of the restroom is a very high level '3', the fall detection device 1000 may express the outline of the second user 1802 with a low degree of definition.

According to an example embodiment, the fall detection device 1000 may detect a dangerous situation of an animal other than a fall of a human. Hereinafter, an operation of the fall detection device 1000 detecting a dangerous situation of a pet will be described in detail with reference to FIG. 19.

Figure 19:
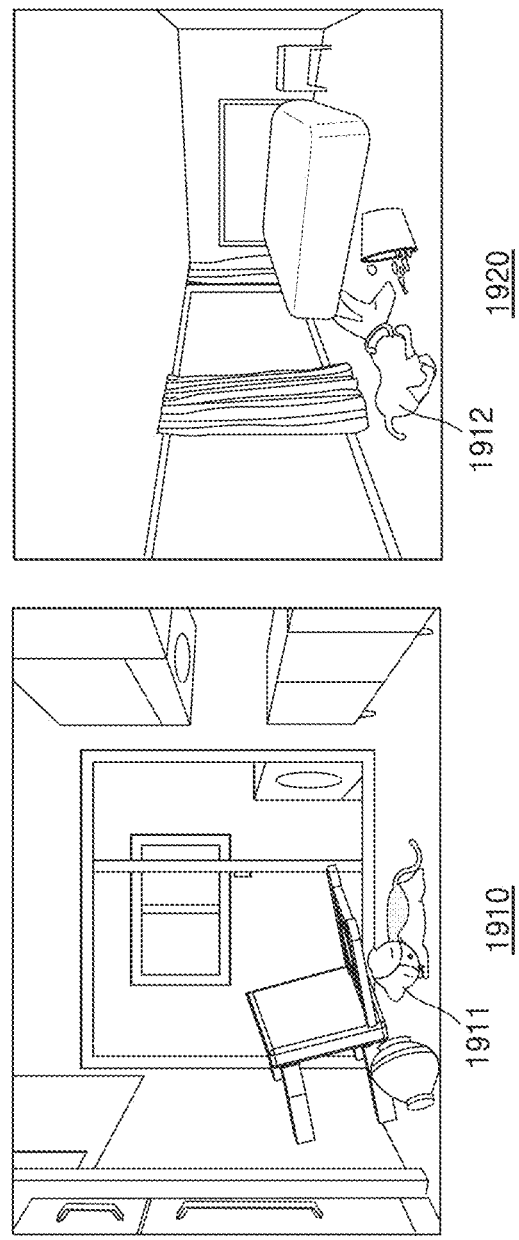
FIG. 19 is a diagram illustrating an operation of detecting a dangerous situation with respect to an animal, according to an example embodiment.

FIG. 19 is a diagram illustrating an operation of detecting a dangerous situation of an animal according to an example embodiment.

Referring to 1910 in FIG. 19, a pet 1911 may climb over a chair and fall since the chair falls. In this case, the fall detection device 1000 may obtain an image of the fallen pet 1911 using the DVS 1100. The fall detection device 1000 may detect an image of the fallen pet 1911 using an appearance model. At this time, the fall detection device 1000 may analyze a series of images of the pet 1911 through a motion model to determine whether the pet 1911 has actually fallen. When it is determined that the pet 1911 has fallen, the fall detection device 1000 may determine a danger of a fall situation based on surrounding environment information or whether the pet 1911 moves after having fallen. If the danger of the fall situation is greater than a threshold value, the fall detection device 1000 may transmit a warning message to an external device (e.g., a mobile phone of a pet owner).

Referring to 1920 of FIG. 19, a pet 1912 may eat wrong food or impurities in a garbage and choke and fall. In this case, the fall detecting device 1000 may obtain an image of the fallen pet 1912 using the DVS 1100. The fall detection device 1000 may detect the image of the fallen pet 1912 using the appearance model. In this case, the fall detection device 1000 may analyze a series of images of the pet 1912 through a motion model to determine whether the pet 1912 is in the dangerous situation. According to an example embodiment, the fall detection device 1000 may use the vibrator 1200 and the DVS 1100 to obtain surrounding environment information (e.g., garbage cans, bed edges, etc.) and determine a danger of the pet 1912 by using the surrounding environment information.

Figure 20:
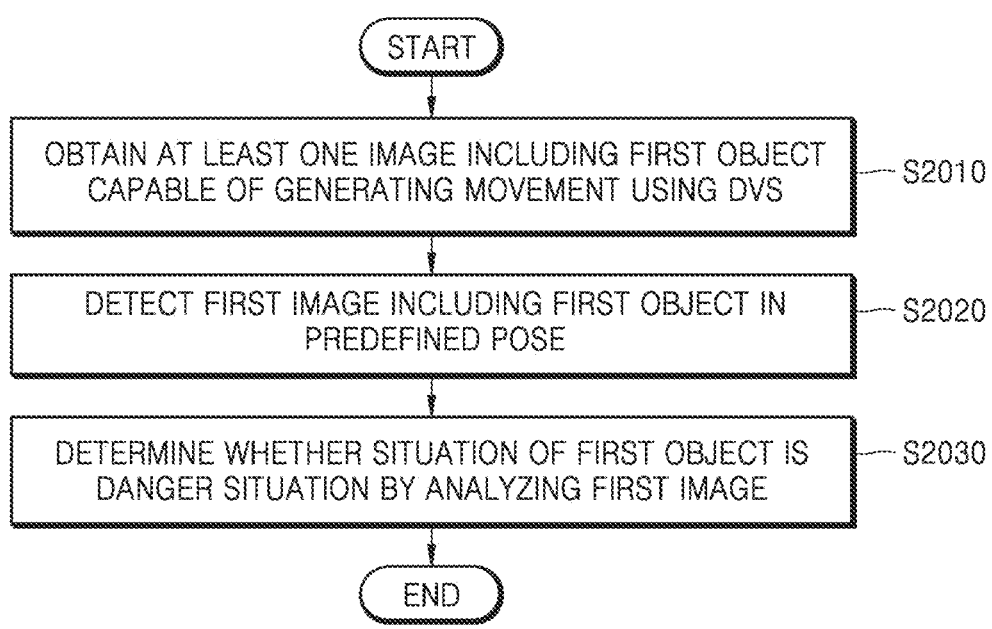
FIG. 20 is a flowchart of a method of detecting a dangerous situation, according to an example embodiment.

FIG. 20 is a flowchart illustrating a method of detecting a dangerous situation according to an example embodiment.

In operation S2010, a danger situation detection device may obtain at least one image including a first object capable of generating a movement, using the DVS 1100.

According to an example embodiment, when the movement of the first object is not detected, the danger situation detection device may obtain an image in a low resolution mode and, when the movement of the first object is not detected, obtain an image in a high resolution mode.

According to an example embodiment, the first object capable of generating the movement may be a person or an animal that is a monitoring target. When the first object moves, the DVS 1100 may capture an image of the first object. At this time, the image of the first object may include an outline, an edge, or a silhouette of the first object.

On the other hand, when the first object moves and another object moves together, not only an outline of the first object but also an outline of the other object may appear in a first image. For example, when the first object rides on a wheelchair and falls with the wheelchair, the outline of the first object and an outline of the wheelchair may appear in the first image.

In operation S2020, the danger situation detection device may detect the first image including the first object in a predefined pose among at least one image. According to an example embodiment, each of the at least one image obtained through the DVS 1100 may be a static image.

According to an example embodiment, the danger situation detection device may analyze the at least one image obtained through the DVS 1100 one by one using a first learning network model. For example, an operation of detecting the first image may be performed by the first learning network model. The first learning network model may be a model learned for analyzing a static image and detecting an image including an object in a predefined pose. The first learning network model may be driven by an artificial intelligence (AI) engine.

According to an example embodiment, when a learning network model (which may be represented by an AI model) uses the at least one image (hereinafter referred to as a DVS image) obtained through the DVS 1100 as learning data, there is an advantage that the learning network model may be lightened because a preprocessing process for an input value is unnecessary compared with the case of using RGB image data as the learning data. For example, if the RGB image data is used as the input value to be input to the learning network model (the AI model), a pre-processing process of extracting movement information between two frames may be required. That is, if the RGB image data is used for determining the danger situation, the preprocessing process (e.g., movement information extraction) may be required to generate data to be input to the learning network model (the AI model). However, when a DVS image is used as the input value to be input to the learning network model (the AI model), since the movement information is included in the DVS image, the preprocessing process for extracting movement information before inputting the DVS image to the learning network model (the AI model) may be unnecessary.

The predefined pose may be a pose associated with a danger situation. According to an example embodiment, the predefined pose may be a pose in which a particular body part (e.g., head, back, chest, knee, heel, palm, etc.) is in contact with a floor (or stairs). For example, the predefined pose may be, but is not limited to, a pose lying with the back on the floor, a pose lying with the belly on the floor, a pose lying with one flank on the floor, a pose leaning against the stairs, and the like. For example, the predefined pose may be a pose wearing a gas mask, a pose holding a fire extinguisher, or a pose pressing an emergency bell.

According to an example embodiment, the danger situation detection device may compensate for a body shape or size of an object included in the static image before analyzing the static image using the learning network model. For example, the danger situation detection device may compensate for a body shape or size of the first object included in the at least one image, taking into consideration at least one of an angle and a position at which the DVS 1100 is installed, and compare the pose of the first object having the compensated body shape or size and the predefined pose.

According to an example embodiment, when it is determined that the first object is partially covered by another object based on the at least one image, the danger situation detection device may move the DVS 1100 with the vibrator 1200, thereby obtaining at least one detailed image including surrounding environment information of the first object from the DVS 1100. The detailed image may also include outlines of peripheral objects (e.g., chairs, desks, beds, drawers, sinks, etc.) where no movement occurs.

According to an example embodiment, the danger situation detection device may detect a second object that covers a part of the first object, based on the at least one detailed image. The danger situation detection device may estimate a pose of the first object partially covered by the second object, considering the second object. At this time, the danger situation detection device may detect the first image by comparing the estimated pose of the first object with the predefined pose.

In operation S2030, the danger situation detection device may analyze the first image to determine whether the situation of the first object is a dangerous situation.

According to an example embodiment, an operation of determining whether the situation of the first object is the dangerous situation may be performed by a second learning network model. According to an example embodiment, the second learning network model may be a learning model of the AI engine that is the same as the first learning network model that detects the first image. Alternatively, the second learning network model may be another learning model of the AI engine that is the same as the first learning network model. Alternatively, the second learning network model may be a learning model of the AI engine that is different from the first learning network model.

According to an example embodiment, when the first object walks using a crutch and falls, the first image may include an image of the crutch as well as an image of the first object. In this case, the danger situation detection device may analyze the first image, determine that the first object falls with the crutch, and determine that the situation of the first object is the dangerous situation.

According to an example embodiment, the danger situation detection device may analyze a plurality of images for the first object including the first image to obtain information about a first movement change of the first object. The danger situation detection device may determine whether the situation of the first object is the fall situation based on the information about the first movement change of the first object. An operation of determining whether the situation of the first object is the fall situation has been described in detail with reference to FIG. 7, and thus a detailed description thereof will be omitted here.

According to an example embodiment, when the situation of the first object is determined to be the dangerous situation, the danger situation detection device may move the DVS 1100 with the vibrator 1200, thereby obtaining at least one detailed image including the surrounding environment information of the first object. In this case, the danger situation detection device may analyze the at least one detailed image to determine the danger of the first object.

For example, as a result of analyzing the detailed image, the danger situation detection device may determine the danger of the first object to a high degree when a staircase exists around the first object, a corner of the desk is present, or a floor is rough. Also, as a result of analyzing the detailed image, when a movement of the first object for a predetermined time is smaller than a threshold value, the danger situation detection device may raise a danger level of the first object.

Figure 21:
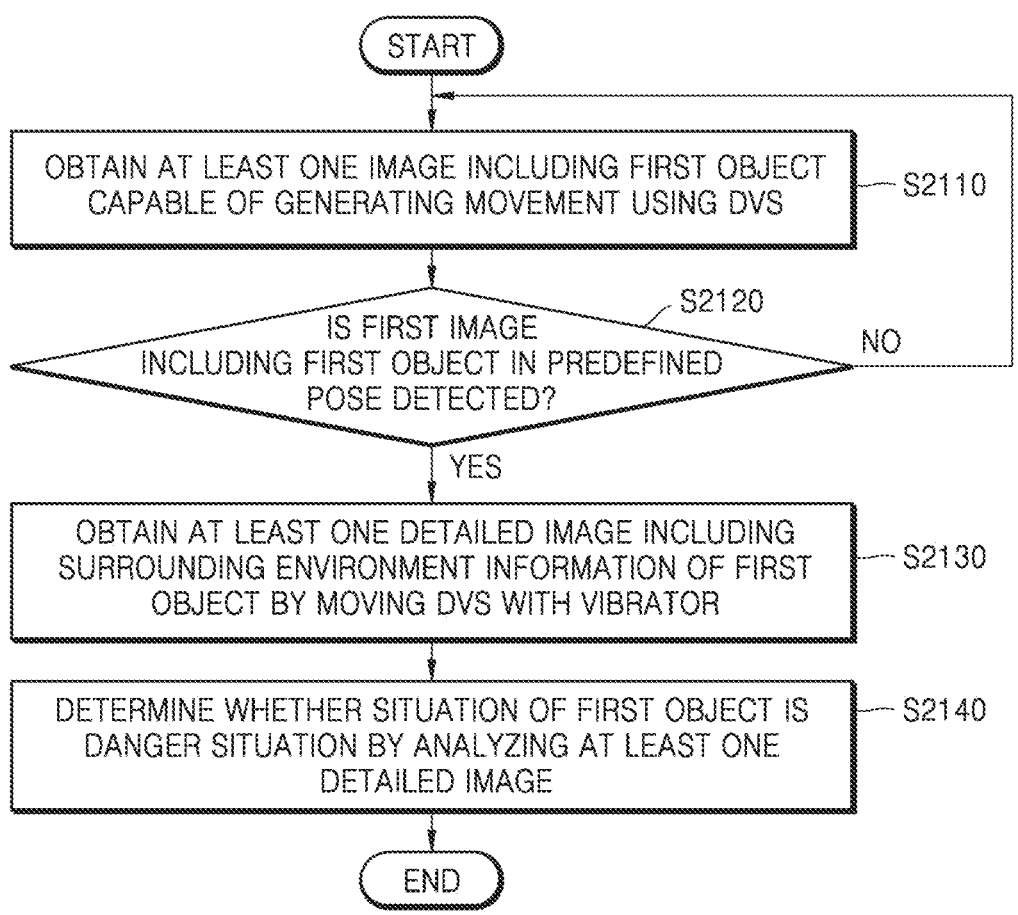
FIG. 21 is a flowchart of a method of detecting a dangerous situation by using detailed images, according to an example embodiment.

FIG. 21 is a flowchart illustrating a method of detecting a dangerous situation using detailed images according to an example embodiment.

In operation S2110, a danger situation detection device may obtain at least one image including a first object capable of generating a movement, using the DVS 1100. Operation S2110 corresponds to operation S2010 in FIG. 20, and thus a detailed description thereof will be omitted.

In operation S2120, the danger situation detection device may detect a first image including the first object in a predefined pose among the at least one image. For example, the danger situation detection device may detect the first image including the first object in a situation of having fallen on a floor. According to an example embodiment, an operation of detecting the first image may be performed by a first learning network model. Operation S2120 corresponds to operation S2020 in FIG. 20, and thus a detailed description thereof will be omitted.

In operation S2130, the danger situation detection device may obtain at least one detailed image including surrounding environment information of the first object by moving the DVS 1100 with the vibrator 1200 when the first image is detected. For example, when the first image of the first object in a pose of having fallen on the floor is detected, the danger situation detection device may move the DVS 1100 to the vibrator 1200 with the vibrator 1200 to obtain a detailed image including information about objects around the first object.

According to an example embodiment, the surrounding environment information of the first object may be information (for example, information about whether other objects exist around the first object, identification information of the other objects existing around the first object, etc.) about other objects around the first object. Thus, the at least one detailed image may include an outline image of the first object and an outline image of the other objects present around the first object. If there are no other objects around the first object, only the outline image of the first object may appear in the detailed image.

In operation S2140, the danger situation detection device may analyze the at least one detailed image to determine whether a situation of the first object is a dangerous situation.

According to an example embodiment, the danger situation detection device may determine whether the situation of the first object is the dangerous situation by using the surrounding environment information (e.g., an object at which the first object falls, a material of the floor, etc.) of the first object. For example, as a result of analyzing the detailed image, the situation of the first object is that the first object falls on a staircase, and hits a first object's head against a staircase rail. In this case, the danger situation detection device may determine that the situation of the first object is the dangerous situation.

According to an example embodiment, an operation of determining whether the situation of the first object is the dangerous situation may be performed by a second learning network model. At this time, the second learning network model may be a learning model of the AI engine that is the same as the first learning network model that detects the first image. Alternatively, the second learning network model may be another learning model of the AI engine that is the same as the first learning network model. Alternatively, the second learning network model may be a learning model of the AI engine that is different from the first learning network model.

According to an example embodiment, when an image including the first object in the predefined pose (for example, a pose falling on the floor) is detected, the danger situation detection device may move a DVS by using a vibrator in order to obtain information about objects that do not move around the first object. In this case, since the moving DVS may also detect detailed images of the objects that do not move around the first object, the danger situation detection device may use the detailed image around the first object to more accurately and objectively determine whether the first object is in a danger situation.

Figure 22:
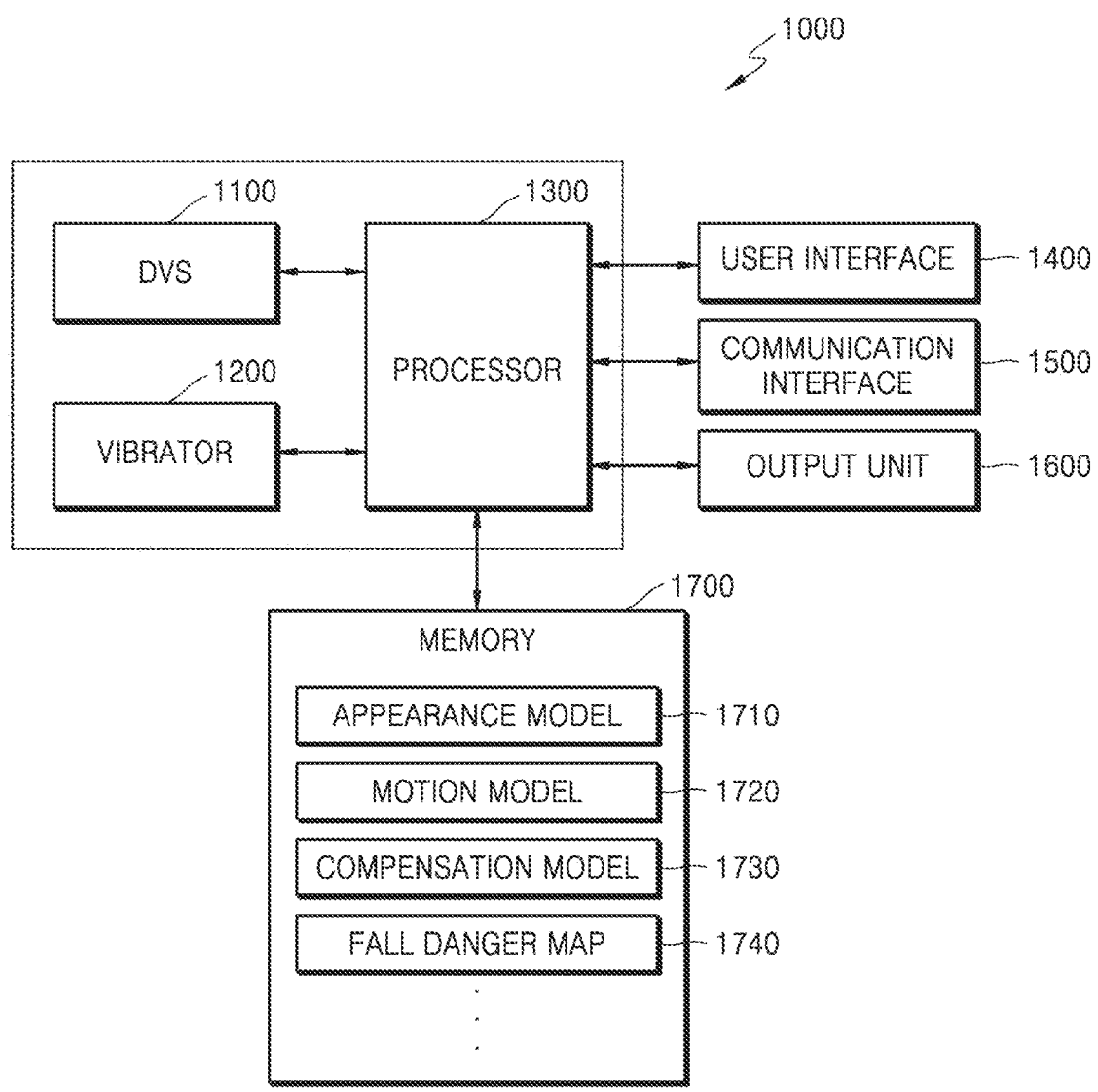
FIG. 22 is a block diagram illustrating a configuration of a fall detection device according to an example embodiment.

FIG. 22 is a block diagram illustrating a configuration of a fall detection device according to an example embodiment.

As shown in FIG. 22, the fall detection device 1000 according to an example embodiment may include the DVS 1100, the vibrator 1200, and a processor 1300. However, not all illustrated components are indispensable components. The fall detection device 1000 may be implemented by more components than the illustrated components. The fall detection device 1000 may be implemented by fewer components than the illustrated components. For example, the fall detection device 1000 may include only the DVS 1100 and the processor 1300, except for the vibrator 1200. The fall detection device 1000 further includes a user interface 1400, a communication interface 1500, an output unit 1600, and a memory 1700 in addition to the DVS 1100, the vibrator 1200, and the processor 1300.

Hereinafter, the components will be described in order.

The DVS 1100 is an image sensor that adopts a way a person's iris receives information and is a sensor capable of obtaining image data of a moving object. For example, the DVS 1100 transmits image data to a processor only when there is a local change in movement in pixel units. That is, the DVS 1100 may transmit image data to the processor only when a moving event occurs. Accordingly, the DVS 1100 does not process data when an object is stopped, may capture the moving object only when the object moves, and transmit data to the processor 1300.

The vibrator 1200 may be a device for generating vibration. For example, the vibrator 1200 may be a vibration motor that outputs a vibration signal. According to an example embodiment, the vibrator 1200 may generate vibrations to move the DVS 1100 artificially. The DVS 1100 is an image sensor useful for movement change detection, but may not obtain information when there is no movement. Accordingly, the vibrator 1200 may artificially move the DVS 1100 so that the DVS 1100 may obtain images of objects even in the absence of movement of the objects.

The DVS 1100 and the vibrator 1200 have been described with reference to FIG. 1, and thus detailed descriptions thereof will be omitted.

The processor 1300 may usually control the overall operation of the fall detection device 1000. For example, the processor 1300 may control the DVS 1100, the vibrator 1200, the user interface 1400, the communication interface 1500, and the output 1600 by executing programs stored in the memory 1700.

According to an example embodiment, the processor 1300 may detect a first image including a first object in a predefined pose from at least one image obtained in the DVS 1100. The predefined pose may be a pose associated with a fall. For example, the predefined pose may be a pose in which a body part (e.g., back, stomach, head, etc.) or a whole of a body touches a floor. For example, when a movement of the first object is detected, the processor 1300 may compare the pose of the first object included in the at least one image with the predefined pose to detect a first image including the first image in the predefined pose.

According to an example embodiment, the processor 1300 may compensate for a body shape or a size of the first object included in the at least one image, taking into account at least one of an angle and a position at which the DVS 1100 is installed. The processor 1300 may detect the first image including the first object in the predefined pose by comparing the pose of the first object having the compensated body shape or size and the predefined pose.

According to an example embodiment, the processor 1300 may control the vibrator 1200 to move the DVS 1100 when it is determined that the first object is partially covered by another object based on the at least one image. The processor 1300 may detect a second object covering a part of the first object based on a fifth image obtained through the moving DVS 1100. The processor 1300 may estimate the pose of the first object partially covered by a second object in consideration of the second object. The processor 1300 may compare the estimated pose of the first object with the predefined pose to detect the first image including the first object in the predefined pose.

The processor 1300 may analyze a plurality of images for the first object including the first image to obtain information about a first movement change of the first object. The plurality of images may include at least one of second images obtained by the DVS 1100 before the first image and third images obtained later than the first image.

The processor 1300 may determine whether a situation of the first object is a fall situation based on information about the first movement change of the first object. For example, the processor 1300 may determine the situation of the first object as the fall situation if similarity between the first movement change of the first object and a second movement change representing a pre-stored fall is greater than a threshold value.

When it is determined that the situation of the first object is the fall situation, the processor 1300 may control the vibrator 1200 to move the DVS 1100 and use fourth images obtained through the moving DVS 1100 to determine a danger of the fall situation. For example, the processor 1300 may analyze the fourth images to obtain surrounding environment information of the first object or fall type information of the first object, and may use the surrounding environment information or the fall type information to determine the danger of the fall situation. According to an example embodiment, the processor 1300 may transmit a warning message to an external device via the communication interface 1500 if the danger of the fall situation is greater than the threshold value.

The processor 1300 may detect a movement of the first object after the situation of the first object is determined to be the fall situation and may raise a danger level of the fall situation if the movement of the first object is less than a threshold value for a predetermined period of time.

The processor 1300 may detect a fall of an object using a deep learning model pre-stored in the memory 1700 or using a deep learning model received from the outside. Also, the processor 1300 may directly generate a deep learning model for detecting the fall. An operation of the processor 1300 directly generating the deep learning model will be described in detail later with reference to FIGS. 21 to 24.

The user interface 1400 refers to a unit for a user to input data for controlling the fall detection device 1000. For example, the user interface 1400 may include a key pad, a dome switch, a touch pad (a contact type capacitance method, a pressure type resistive method, an infrared ray detection method, a surface ultrasonic wave conduction method, an integral type tension measuring method, a piezo effect method, etc.), a jog wheel, a jog switch, and the like, but is not limited thereto.

The user interface 1400 may receive an input that sets a privacy level of a space in which the DVS 1100 is installed. Alternatively, the user interface 1400 may receive an input that sets a degree of definition of an image obtained via the DVS 1100.

The communication interface 1500 includes at least one component for enabling communication between the fall detection device 1000 and the server 2000, between the fall detection device 1000 and the wearable device 3000, and between the fall detection device 1000 and a mobile terminal. For example, the communication interface 1500 may include a short-range wireless communication unit, a mobile communication unit, and the like.

The short-range wireless communication unit may include a Bluetooth communication unit, a Bluetooth low energy (BLE) communication unit, a near field communication unit, a WLAN communication unit, a Zigbee communication unit, an infrared data association (IrDA) communication unit, a Wi-Fi Direct (WFD) communication unit, an ultra wideband (UWB) communication unit, an Ant+ communication unit, and the like.

The mobile communication unit transmits and receives a wireless signal to and from at least one of a base station, an external terminal, and a server on a mobile communication network. Here, the wireless signal may include a voice call signal, a video call signal, or various types of data depending on text/multimedia message transmission/reception. In this case, the mobile communication unit may use at least one of a long-term evolution (LTE), a LTE Advance (LTE-A), a code division multiple access (CDMA), a wideband CDMA (WCDMA), a universal mobile telecommunications system (UMTS), and a WiBro And Global System for Mobile Communications (GSM).

The output unit 1600 is for outputting a video signal, an audio signal, or a vibration signal, and may include a display, an acoustic output unit, a vibration motor, and the like.

The display may display information processed in the fall detection device 1000. For example, the display may display an image obtained through the DVS 1100, a preview image, a moving image file list, a moving image reproduction screen, and the like.

When the display and the touch pad have a layer structure and are configured as a touch screen, the display may be used as an input device in addition to an output device. The display may include at least one of a liquid crystal display, a thin film transistor-liquid crystal display, an organic light-emitting diode, a flexible display, a three-dimensional (3D) display, and an electrophoretic display.

The audio output unit outputs audio data received from the communication interface 1500 or stored in the memory 1700. Also, the sound output unit outputs an acoustic signal related to a function (e.g., of generating a warning message) performed in the fall detection device 1000. The sound output unit may include a speaker, a buzzer, and the like.

The memory 1700 may store a program for processing and controlling the processor 1300 and may store input/output data (e.g., static images, moving images, etc.)

The memory 1700 may include, for example, an internal memory or an external memory. The internal memory may include at least one of, for example, a volatile memory such as a dynamic RAM (DRAM), a static RAM (SRAM), or a synchronous dynamic RAM (SDRAM), a non-volatile memory such as an OTPROM time programmable ROM (ROM), programmable ROM (PROM), erasable and programmable ROM (EPROM), electrically erasable and programmable ROM (EEPROM), mask ROM, flash ROM, flash memory (such as NAND flash or NOR flash) and a solid situation drive (SSD).

The external memory may include a flash drive such as a compact flash (CF), a secure digital (SD), a micro secure digital (SD), a mini secure digital (SD), an extreme digital (xD), a multi-media card (MMC), a memory stick, or the like. The external memory may be functionally and/or physically connected to the fall detection device 1000 through various interfaces.

Also, the fall detection device 1000 may operate a web storage that performs a storage function of the memory 1700 on the Internet.

Programs stored in the memory 1700 may be classified into a plurality of modules according to their functions. For example, the programs may be classified into the appearance model 1710, a motion model 1720, a compensation model 1730, a fall danger map model 1740, and the like. According to an example embodiment, the memory 1700 may store the fall danger map 600.

The appearance model 1710 may be a model learned to analyze static images one by one to detect a body shape or a pose of an object included in the static image and determine whether the detected body shape or pose of the object is similar to a predefined pose in relation to a fall.

The motion model 1720 may be a model learned to analyze a plurality of images (e.g., moving images) to detect a movement pattern of the object and to determine whether the detected movement pattern of the object is similar to a movement pattern representing the fall. In general, since the motion model 1720 stacks (for example, N images stacking) and processes multiple images, the motion model 1720 takes N times longer than the appearance model 1710 that processes a single image.

The compensation model 1730 may be a model learned to compensate for a size, a shape, or occlusion of an object included in the image obtained through the DVS 1100.

The fall danger map 600 may be a map indicating a region that may be dangerous when the fall occurs.

Hereinafter, an operation of generating an appearance model, the motion model 1720, the compensation model 1730, and the like as a learning model for detecting a fall of the processor 1300 will be described with reference to FIG. 23.

Figure 23:
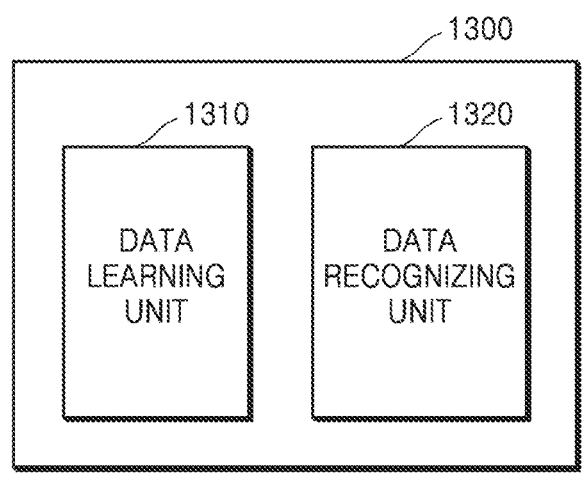
FIG. 23 is a block diagram of a processor according to an example embodiment.

FIG. 23 is a block diagram of the processor 1300 according to an example embodiment.

Referring to FIG. 23, the processor 1300 according to one or more example embodiments may include a data learning unit 1310 and a data recognizing unit 1320.

The data learning unit 1310 may learn a reference for determining a dangerous situation (for example, a fall situation). The data learning unit 1310 may learn the reference about what data used to determine the fall situation and how to determine a situation using data. The data learning unit 1310 may obtain data (for example, images) to be used for learning and apply the obtained data to a data recognition model to be described later to learn the reference for determining the fall situation.

According to an example embodiment, the data learning unit 1310 may learn a daily behavior or a fall behavior of an object (a person or an animal) at a specific illumination (e.g., a general illumination or a low illumination). According to an example embodiment, the data learning unit 1310 may learn the daily behavior or the fall behavior according to a body characteristic (for example, age, sex, etc.) of the object. For example, the data learning unit 1310 may learn fall patterns in various situations such as a fall pattern of a child, a fall pattern of an elderly person, a fall pattern of a person using a walker, a fall pattern of a person using crutches, a fall pattern during carrying goods, etc.

According to an example embodiment, the data learning unit 1310 may learn a reference for recognizing an object. For example, the data learning unit 1310 may learn human characteristics, pet characteristics, furniture characteristics, object characteristics, and the like.

According to an example embodiment, the data learning unit 1310 may learn a place image for determining a place. Also, the data learning unit 1310 may learn a correlation between an object and the place detected in the place image. For example, the data learning unit 1310 may learn a correlation between a sofa, a television, and the like detected in a living room image and a living room.

According to an example embodiment, when a first object is covered by a second object, the data learning unit 1310 may learn an image for compensating for the covered first object. For example, the data learning unit 1310 may learn an image for compensating for a case where a person is covered by furniture. Further, according to an example embodiment, the data learning unit 1310 may learn distortion data for compensating for a distortion caused by a camera lens.

The data recognition unit 1320 may determine a fall situation based on data. The data recognition unit 1320 may recognize the fall situation from detected data by using a learned data recognition model. The data recognition unit 1320 may obtain image data according to a preset reference by learning (for example, obtaining image data from the DVS 1100), and use a data recognition model that uses the obtained image data as an input value to determine the fall situation based on the image data. Further, a resultant value output by the data recognition model by using the obtained image data as the input value may be used to update the data recognition model.

At least one of the data learning unit 1310 and the data recognition unit 1320 may be manufactured in at least one hardware chip type and may be mounted on the fall detection device 1000. For example, at least one of the data learning unit 1310 and the data recognition unit 1320 may be manufactured in a dedicated hardware chip type for artificial intelligence (AI) or an existing general purpose processor (for example: a CPU or an application processor) or a graphics processor (e.g., a GPU) and mounted on the fall detection device 1000.

The data learning unit 1310 and the data recognition unit 1320 may be mounted on the single fall detection device 1000, or may be respectively mounted on separate fall detection devices. For example, one of the data learning unit 1310 and the data recognition unit 1320 may be included in the fall detecting device 1000, and the other may be included in the server 2000. Further, the data learning unit 1310 and the data recognition unit 1320 may provide model information built by the data learning unit 1310 to the data recognition unit 1320 by wired or wirelessly. Data input to the data recognition unit 1320 may be provided to the data learning unit 1310 as additional learning data.

Meanwhile, at least one of the data learning unit 1310 and the data recognition unit 1320 may be implemented as a software module. When at least one of the data learning unit 1310 and the data recognition unit 1320 is implemented as the software module (or a program module including an instruction), the software module may be stored in non-transitory computer readable media. Further, in this case, one or more software modules may be provided by an operating system (OS) or by a predetermined application. Alternatively, some of the one or more software modules may be provided by the OS, and the other software modules may be provided by the predetermined application.

Figure 24:
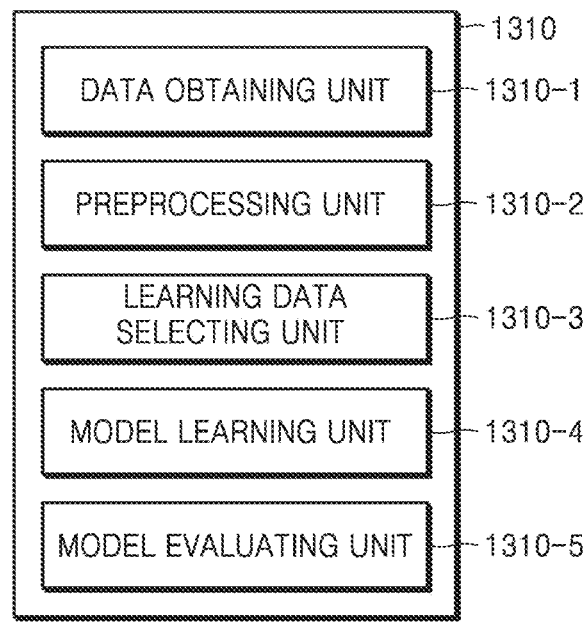
FIG. 24 is a block diagram of a data learning unit according to an example embodiment.

FIG. 24 is a block diagram of the data learning unit 1310 according to an example embodiment.

Referring to FIG. 24, the data learning unit 1310 according to an example embodiment may include a data obtaining unit 1310-1, a preprocessing unit 1310-2, a learning data selecting unit 1310-3, a model learning unit 1310-4, and a model evaluating unit 1310-5.

The data obtaining unit 1310-1 may obtain data necessary for determining a fall situation. The data obtaining unit 1310-1 may obtain data (e.g., images) necessary for learning for determining the fall situation. According to an example embodiment, the data obtaining unit 1310-1 may directly generate the data necessary for determining the fall situation or may receive the data necessary for determining the fall situation from an external device or a server.

According to an example embodiment, the data necessary for determining the fall situation may include image data including an object in a predefined pose relating to a fall, moving image data including a movement pattern representing the fall, context information about a surrounding environment for determining a danger of the fall, etc. but it is not limited thereto.

According to an example embodiment, the data obtaining unit 1310-1 may receive a static image or a moving image captured through a DVS. The moving image may be composed of a plurality of images (or frames). For example, the data obtaining unit 1310-1 may receive the moving image through the DVS 1100 of the fall detection device 1000 including the data learning unit 1310 or an external fall detection device capable of communicating with the fall detection device 1000 including the data learning unit 1310.

According to an example embodiment, the data obtaining unit 1310-1 may obtain image data, voice data, text data, biometric signal data, and the like. For example, the data obtaining unit 1310-1 may receive data through an input device (e.g., a microphone, a camera, a sensor, or the like) of the fall detection device 1000. Alternatively, the data obtaining unit 1310-1 may obtain the data through an external device communicating with the fall detection device 1000.

The preprocessing unit 1310-2 may pre-process the obtained data so that the obtained data may be used for learning for determining the fall situation. The preprocessing unit 1310-2 may process the obtained data into a predetermined format so that the model learning unit 1310-4, which will be described later, may use the data obtained for learning for determining the fall situation.

For example, the preprocessing unit 1310-2 may overlap at least a part of a plurality of images to generate a single composite image based on a common region included in each of the plurality of images (or frames) constituting at least a part of the input moving image. In this case, a plurality of composite images may be generated from a single moving image. The common region may be a region including the same or similar common object (e.g., an object, animal, plant, or person, etc.) in each of the plurality of images. Alternatively, the common region may be a region that is the same or similar in a color, a shade, an RGB value or a CMYK value in each of the plurality of images.

The learning data selecting unit 1310-3 may select data necessary for learning from the preprocessed data. The selected data may be provided to the model learning unit 1310-4. The learning data selecting unit 1310-3 may select the data necessary for learning from the preprocessed data according to a predetermined reference for determining the fall situation. The learning data selecting unit 1310-3 may also select the data according to a predetermined reference by learning by the model learning unit 1310-4, which will be described later. For example, the learning data selecting unit 1310-3 may select image data including an object related to a fall (e.g., a pose in which a part of a person's body touches the ground (for example, a back lying pose, a belly lying pose, etc.).

The model learning unit 1310-4 may learn a reference about how to determine the fall situation based on the learning data. Also, the model learning unit 1310-4 may learn a reference for determining which learning data should be used for determining the fall situation.

Also, the model learning unit 1310-4 may learn a data recognition model used for determining the fall situation using the learning data. In this case, the data recognition model may be a pre-built model. For example, the data recognition model may be a pre-built model that receives basic learning data (e.g., a sample image, etc.).

The data recognition model may be constructed in consideration of an application field of a recognition model, a purpose of learning, or a computer performance of a device. The data recognition model may be, for example, a model based on a neural network. For example, the data recognition model may use models such as Deep Neural Network (DNN), Recurrent Neural Network (RNN), and Bidirectional Recurrent Deep Neural Network (BRDNN), but is not limited thereto.

According to various example embodiments, when there are a plurality of data recognition models that are built in advance, the model learning unit 1310-4 may determine a data recognition model having a high relation between input learning data and basic learning data as the data recognition model to learn. In this case, the basic learning data may be previously classified according to data types, and the data recognition model may be previously built according to data types. For example, the basic learning data may be previously classified by various references such as a region where the learning data is generated, a time at which the learning data is generated, a size of the learning data, a genre of the learning data, a creator of the learning data, a type of an object in the learning data, etc.

Also, the model learning unit 1310-4 may learn the data recognition model using, for example, a learning algorithm including an error back-propagation method or a gradient descent method.

Also, the model learning unit 1310-4 may learn the data recognition model through supervised learning using, for example, learning data as an input value. Also, the model learning unit 1310-4 may learn for itself, for example, a type of data necessary for determining a situation without any guidance, thereby learning the data recognition model through unsupervised learning to find a reference for determining the situation. Also, the model learning unit 1310-4 may learn the data recognition model through reinforcement learning using, for example, feedback on whether a result of determining the situation based on learning is correct.

Further, when the data recognition model is learned, the model learning unit 1310-4 may store the learned data recognition model. In this case, the model learning unit 1310-4 may store the learned data recognition model in the memory 1700 of the fall detection device 1000 including the data recognizing unit 1320. Alternatively, the model learning unit 1310-4 may store the learned data recognition model in the memory 1700 of the fall detection device 1000 including the data recognizing unit 1320 that will be described later. Alternatively, the model learning unit 1310-4 may store the learned data recognition model in a memory of the server 2000 connected to the fall detection device 1000 over a wired or wireless network.

In this case, the memory in which the learned data recognition model is stored may also store, for example, a command or data associated with at least one other component of the fall detection device 1000. The memory may also store software and/or programs. The program may include, for example, a kernel, a middleware, an application programming interface (API), and/or an application program (or an application), etc.

The model evaluating unit 1310-5 may input evaluation data to the data recognition model, and if a recognition result output from the evaluation data does not satisfy a predetermined reference, allow the model learning unit 1310-4 to learn again. In this case, the evaluation data may be predetermined data for evaluating the data recognition model.

For example, when the number or percentage of the evaluation data whose recognition result is not correct exceeds a predetermined threshold value in the recognition result of the learned data recognition model for the evaluation data, the model evaluating unit 1310-5 may evaluate the learned data recognition model as being unsatisfactory. For example, when a predetermined reference is defined as a percentage of 2%, when the learned data recognition model outputs an incorrect recognition result for evaluation data exceeding 20 out of a total of 1000 pieces of evaluation data, the model evaluating unit 1310-5 may evaluate the learned data recognition model as being unsuitable.

On the other hand, when there are a plurality of learned data recognition models, the model evaluating unit 1310-5 may evaluate whether each of learned moving image recognition models satisfies a predetermined reference, and may determine a model satisfying the predetermined reference as a final data recognition model. In this case, when there are a plurality of models satisfying the predetermined reference, the model evaluating unit 1310-5 may determine any one or a predetermined number of models previously set in descending order of evaluation scores as the final data recognition model.

At least one of the data obtaining unit 1310-1, the preprocessing unit 1310-2, the learning data selecting unit 1310-3, the model learning unit 1310-4, and the model evaluating unit 1310-4 in the data learning unit 1310 may be manufactured in at least one hardware chip type and mounted on the fall detection device 1000. For example, at least one of the data obtaining unit 1310-1, the preprocessing unit 1310-2, the learning data selecting unit 1310-3, the model learning unit 1310-4, and the model evaluating unit 1310-5 may be manufactured in a dedicated hardware chip type for artificial intelligence (AI) or an existing general purpose processor (for example: a CPU or an application processor) or a graphics processor (e.g., a GPU) and mounted on the fall detection device 1000.

The data obtaining unit 1310-1, the preprocessing unit 1310-2, the learning data selecting unit 1310-3, the model learning unit 1310-4, and the model evaluating unit 1310-5 may be mounted on the fall detection device 1000, or may be mounted on separate fall detection devices, respectively. For example, some of the data obtaining unit 1310-1, the preprocessing unit 1310-2, the learning data selecting unit 1310-3, the model learning unit 1310-4, and the model evaluating unit 1310-5 may be included in the fall detection device 1000, and the others may be included in the server 2000.

Also, at least one of the data obtaining unit 1310-1, the preprocessing unit 1310-2, the learning data selecting unit 1310-3, the model learning unit 1310-4, and the model evaluating unit 1310-5 may be implemented as a software module. When at least one of the data obtaining unit 1310-1, the preprocessing unit 1310-2, the learning data selecting unit 1310-3, the model learning unit 1310-4, and the model evaluating unit 1310-5 is implemented as the software module (or a program module including an instruction), the software module may be stored in non-transitory computer readable media. Further, in this case, one or more software modules may be provided by an operating system (OS) or by a predetermined application. Alternatively, some of the one or more software modules may be provided by the OS and the others may be provided by the predetermined application.

Figure 25:
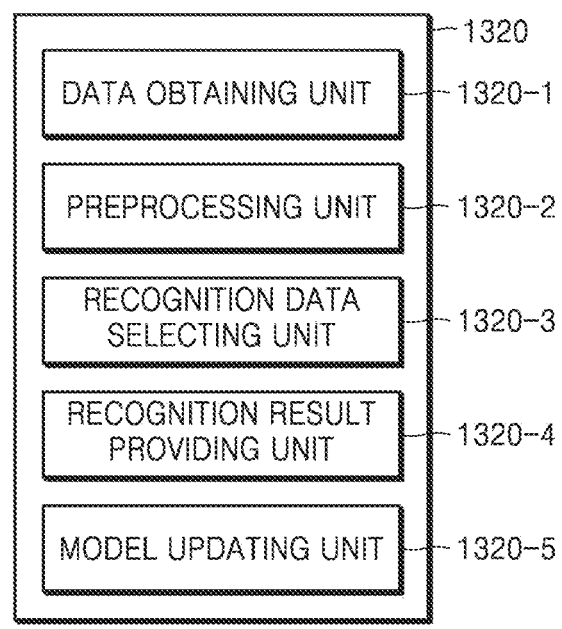
FIG. 25 is a block diagram of a data recognizing unit according to an example embodiment.

FIG. 25 is a block diagram of the data recognizing unit 1320 according to an example embodiment.

Referring to FIG. 25, a data recognition unit 1320 according to an example embodiment may include a data obtaining unit 1320-1, a preprocessing unit 1320-2, a recognition data selecting unit 1320-3, a recognition result providing unit 1320-4, and a model updating unit 1320-5.

The data acquisition unit 1320-1 may obtain data necessary for determining a fall situation. The preprocessing unit 1320-2 may preprocess the obtained data such that the data obtained for determining the fall situation may be used. The preprocessing unit 1320-2 may process the obtained data into a predetermined format so that the recognition result providing unit 1320-4, which will be described later, may use the data obtained for determining the fall situation.

The recognition data selecting unit 1320-3 may select data necessary for determining the fall situation from the preprocessed data. The selected data may be provided to the recognition result provider 1320-4. The recognition data selecting unit 1320-3 may select some or all of the preprocessed data according to a predetermined reference for determining the fall situation. The recognition data selecting unit 1320-3 may also select the data according to a predetermined reference by learning by the model learning unit 1310-4 which will be described later.

The recognition result providing unit 1320-4 may apply the selected data to a data recognition model to determine the situation. The recognition result providing unit 1320-4 may provide a recognition result according to a data recognition purpose. The recognition result providing unit 1320-4 may apply the selected data to the data recognition model by using the data selected by the recognition data selecting unit 1320-3 as an input value. Also, the recognition result may be determined by the data recognition model.

For example, a recognition result of at least one image may be provided as text, voice, a moving image, an image or a command (for example, an application execution command, a module function execution command, etc.). For example, the recognition result providing unit 1320-4 may provide a recognition result of an object included in the at least one image. The recognition result may be, for example, pose information of the object included in the at least one image, surrounding situation information of the object, movement change information of an object included in a moving image, and the like. The recognition result providing unit 1320-4 may provide the 'fall situation' as text, voice, an image, a command or the like as situation information of the object.

The model updating unit 1320-5 may update the data recognition model based on an evaluation of the recognition result provided by the recognition result providing unit 1320-4. For example, the model updating unit 1320-5 may provide the model learning unit 1310-4 with the recognition result provided by the recognition result providing unit 1320-4 so that the model learning unit 1310-4 may update the data recognition model.

Meanwhile, at least one of the data obtaining unit 1320-1, the preprocessing unit 1320-2, the recognition data selecting unit 1320-3, the recognition result providing unit 1320-4, and the model updating unit 1320-5 in the data recognizing unit 1320 may be manufactured in at least one hardware chip type and mounted on the fall detection device 1000. For example, at least one of the data obtaining unit 1320-1, the preprocessing unit 1320-2, the recognition data selecting unit 1320-3, the recognition result providing unit 1320-4, and the model updating unit 1320-5 may be manufactured in a dedicated hardware chip type for artificial intelligence (AI) or an existing general purpose processor (for example: a CPU or an application processor) or a graphics processor (e.g., a GPU) and mounted on the fall detection device 1000.

The data obtaining unit 1320-1, the preprocessing unit 1320-2, the recognition data selecting unit 1320-3, the recognition result providing unit 1320-4, and the model updating unit 1320-5 may be mounted on the fall detection device 1000, or may be mounted on separate fall detection devices, respectively. For example, some of the data obtaining unit 1320-1, the preprocessing unit 1320-2, the recognition data selecting unit 1320-3, the recognition result providing unit 1320-4, and the model updating unit 1320-5 may be included in the fall detection device 1000, and the others may be included in the server 2000.

Also, at least one of the data obtaining unit 1320-1, the preprocessing unit 1320-2, the recognition data selecting unit 1320-3, the recognition result providing unit 1320-4, and the model updating unit 1320-5 may be implemented as a software module. When at least one of the data obtaining unit 1320-1, the preprocessing unit 1320-2, the recognition data selecting unit 1320-3, the recognition result providing unit 1320-4, and the model updating unit 1320-5 is implemented as the software module (or a program module including an instruction), the software module may be stored in non-transitory computer readable media. Further, in this case, one or more software modules may be provided by an operating system (OS) or by a predetermined application. Alternatively, some of the one or more software modules may be provided by the OS and the others may be provided by the predetermined application.

Figure 26:
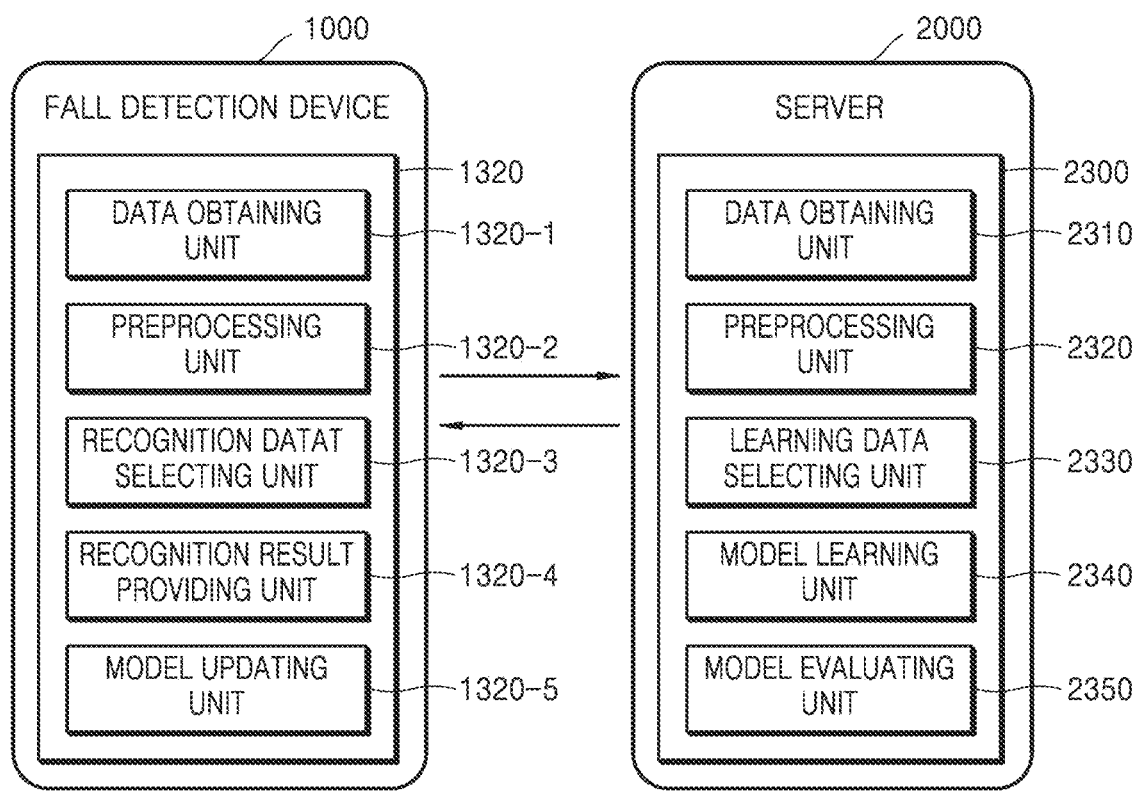
FIG. 26 is a diagram illustrating an example in which a fall detection device and a server interact with each other to learn and recognize data, according to an example embodiment.

FIG. 26 is a diagram illustrating an example in which the fall detection device 1000 and the server 2000 interact with each other to learn and recognize data according to an example embodiment.

Referring to FIG. 26, the server 2000 may learn a reference for determining a fall situation, and the fall detection device 1000 may determine the fall situation based on a learning result by the server 2000.

The server 2000 may include a data learning unit 2300 according to an example embodiment, which may include a data obtaining unit 2310, a preprocessing unit 2320, a learning data selecting unit 2330, a model learning unit 2340, and a model evaluating unit 2350.

The model learning unit 2340 of the server 2000 may perform a function of the data learning unit 1310 shown in FIG. 24. The model learning unit 2340 of the server 2000 may learn a reference about what data is used to determine the fall situation and how to determine the fall situation using the data. The model learning unit 2340 may obtain data to be used for learning, and apply the obtained data to a data recognition model that will be described later, thereby learning the reference for determining the fall situation.

Also, the recognition result providing unit 1320-4 of the fall detection device 1000 may apply the data selected by the recognition data selecting unit 1320-3 to the data recognition model generated by the server 2000 to determine the situation. For example, the recognition result providing unit 1320-4 may transmit the data selected by the recognition data selecting unit 1320-3 to the server 2000, and may request the server 2000 to apply the data selected by the recognition data selecting unit 1320-3 to the recognition model and determine the situation. Also, the recognition result providing unit 1320-4 may receive, from the server 2000, information about the situation determined by the server 2000.

Alternatively, the recognition result providing unit 1320-4 of the fall detection device 1000 may receive the recognition model generated by the server 2000 from the server 2000 and determine the fall situation using the received recognition model. In this case, the recognition result providing unit 1320-4 of the fall detection device 1000 may apply the data selected by the recognition data selecting unit 1320-3 to the data recognition model received from the server 2000 to determine the fall situation.

The method according to an example embodiment may be implemented as computer instructions which may be executed by various computer means, and recorded on a non-transitory computer-readable recording medium. The non-transitory computer-readable recording medium may include program commands, data files, data structures, or a combination thereof. The program commands recorded on the non-transitory computer-readable recording medium may be specially designed and constructed for the present disclosure or may be known to and usable by one of ordinary skill in a field of computer software. Examples of the non-transitory computer-readable medium include magnetic media such as hard discs, floppy discs, or magnetic tapes, optical media such as compact disc-read only memories (CD-ROMs), or digital versatile discs (DVDs), magneto-optical media such as floptical discs, and hardware devices that are specially configured to store and carry out program commands, such as ROMs, RAMs, or flash memories. Examples of the program commands include a high-level programming language that may be executed by a computer using an interpreter as well as a machine language code made by a complier.

Example embodiments may be implemented in a form of a recording medium including computer-executable instructions such as a program module executed by a computer system. A non-transitory computer-readable medium may be an arbitrary available medium which may be accessed by a computer system and includes all types of volatile and non-volatile media and separated and non-separated media. Also, the non-transitory computer-readable medium may include all types of computer storage media and communication media. The computer storage media include all types of volatile and non-volatile and separated and non-separated media implemented by an arbitrary method or technique for storing information such as computer-readable instructions, a data structure, a program module, or other data. The communication media typically include computer-readable instructions, a data structure, a program module, other data of a modulated signal such as a carrier, other transmission mechanism, and arbitrary information delivery media. Also, example embodiments may also be implemented by a computer program including computer-executable instructions, such as a computer program to be executed by a computer, or a computer program product.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the figures, it will be understood by those of ordinary skill in the art that various changes in form and details may be made therein without departing from the spirit and scope as defined by the following claims.

What is claimed is:

1. A method of detecting a dangerous situation, the method comprising:
   obtaining static images each comprising a first object capable of generating a movement, by using a dynamic vision sensor (DVS);
   analyzing the static images one by one, wherein the analyzing of the static images one by one comprises:
      analyzing a first static image from among the static images by determining whether a pose of the first object in the first static image corresponds to a predefined pose, and
      in response to determining that the pose of the first object in the first static image does not correspond to the predefined pose, proceeding to analyze a next static image from among the static images;
   based on only when it is determined that the pose of the first object in the first static image corresponds to the predefined pose, obtaining information about a first movement variation of the first object by analyzing a plurality of images from among the static images, the plurality of images including the first static image; and
   determining whether a situation of the first object is the dangerous situation based on the information about the first movement variation of the first object.

2. The method of claim 1, wherein the detecting of the first static image and the determining of whether the situation of the first object is the dangerous situation are performed by a neural network model.

3. The method of claim 2, wherein the detecting of the first static image comprises:
   in response to the movement of the first object being detected, comparing a pose of the first object included in the static images with the predefined pose by using the neural network model; and
   detecting the first static image based on a result of the comparing.

4. The method of claim 1, further comprising:
   in response to the situation of the first object being determined to be the dangerous situation, obtaining at least one detailed image comprising surrounding environment information of the first object generated by vibrating the DVS with a vibrator, wherein the at least one detailed image includes non-moving objects around the first object; and
   determining a degree of a danger of the first object by analyzing the at least one detailed image.

5. The method of claim 4, wherein the determining of the danger of the first object comprises:
   in response to determining that the movement of the first object is less than a threshold value for a predetermined time, raising a danger level of the first object.

6. The method of claim 1, wherein the determining of whether the situation of the first object is the dangerous situation comprises:
   determining whether the situation of the first object is a fall situation based on the information about the first movement variation of the first object.

7. The method of claim 1, wherein the detecting of the first image comprises:
   compensating for a body shape of the first object or a size of the first object included in the static images, by adjusting for at least one from among an angle and a position at which the DVS is installed; and
   comparing a pose of the first object having the compensated body shape or size with the predefined pose.

8. The method of claim 1, wherein the detecting of the first static image comprises:
in response to determining that the first object is partially covered by another object, obtaining at least one detailed image comprising surrounding environment information of the first object generated by moving the DVS with a vibrator;
detecting, based on the at least one detailed image, a second object covering a part of the first object in the at least one detailed image; and
estimating a pose of the first object partially covered by the second object by adjusting for the second object.

9. The method of claim 1, wherein the obtaining of the static images comprise:
adjusting a degree of definition of the first object included in the static images according to a privacy level of a space in which the DVS is installed.

10. The method of claim 1, wherein the obtaining of the static images comprise:
obtaining the static images in a high resolution mode in response to the movement of the first object being detected; and
obtaining the static images in a low resolution mode in response to the movement of the first object not being detected.

11. A device for detecting a dangerous situation, the device comprising:
a dynamic vision sensor (DVS) configured to obtain static images each comprising a first object capable of generating a movement; and
a processor configured to:
analyze the static images one by one, wherein the analyzing of the static images one by one comprises:
analyzing a first static image from among the static images by determining whether a pose of the first object in the first static image corresponds to a predefined pose, and
in response to determining that the pose of the first object in the first static image does not correspond to the predefined pose, proceeding to analyze a next static image from among the static images;
only when it is determined that the pose of the first object in the first static image corresponds to the predefined pose, obtain information about a first movement variation of the first object by analyzing a plurality of images from among the static images, the plurality of images including the first static image, and
determine whether a situation of the first object is the dangerous situation based on the information about the first movement variation of the first object.

12. The device of claim 11, wherein the processor is further configured to detect the first static image by using a neural network model, and determine whether the situation of the first object is the dangerous situation by using the neural network model.

13. The device of claim 11, further comprising a vibrator configured to move the DVS,
wherein the processor is further configured to:
control the vibrator to vibrate the DVS in response to determining that the situation of the first object is the dangerous situation;
obtain at least one detailed image comprising surrounding environment information of the first object generated by vibrating the DVS, wherein the at least one detailed image includes non-moving objects around the first object; and
analyze the at least one detailed image to determine a degree of a danger of the first object.

14. The device of claim 13, wherein the processor is further configured to raise a danger level of the first object in response to determining that a movement of the first object is less than a threshold value for a predetermined time.

15. The device of claim 11, wherein the processor is further configured to compensate for a body shape of the first object or a size of the first object included in the static images, by adjusting for at least one from among an angle and a position at which the DVS is installed, and compare a pose of the first object having the compensated body shape or size with the predefined pose to detect the first static image.

16. The device of claim 11, further comprising a vibrator configured to move the DVS,
wherein the processor is further configured to:
obtain at least one detailed image comprising surrounding environment information of the first object generated by moving the DVS with the vibrator in response to determining that the first object is partially covered by another object;
detect a second object covering a part of the first object, based on the at least one detailed image; and
estimate a pose of the first object partially covered by the second object by adjusting for the second object.

17. A non-transitory computer-readable storage medium storing instructions for causing a computer to:
obtain static images comprising a first object capable of generating a movement, by using a dynamic vision sensor (DVS);
analyze the static images one by one, wherein the analyzing of the static images one by one comprises:
analyzing a first static image from among the static images by determining whether a pose of the first object in the first static image corresponds to a predefined pose, and
in response to determining that the pose of the first object in the first static image does not correspond to the predefined pose, proceeding to analyze a next static image from among the static images;
only when it is determined that the pose of the first object in the first static image corresponds to the predefined pose, obtain information about a first movement variation of the first object by analyzing a plurality of images from among the static images, the plurality of images including the first static image; and
determine whether a situation of the first object is a dangerous situation based on the information about the first movement variation of the first object.

* * * * *